US009216952B2

(12) United States Patent
Califano et al.

(10) Patent No.: US 9,216,952 B2
(45) Date of Patent: Dec. 22, 2015

(54) PROCESS FOR PREPARING ANTIVIRAL COMPOUND

(75) Inventors: Jean-Christophe Califano, Whitefish Bay, WI (US); James J. Napier, Antioch, IL (US); Calvin L. Becker, Kenosha, WI (US); Su Yu, Lake Bluff, IL (US)

(73) Assignee: AbbVie Inc., North Chicago, IL (US)

( * ) Notice: Subject to any disclaimer, the term of this patent is extended or adjusted under 35 U.S.C. 154(b) by 489 days.

(21) Appl. No.: 13/070,142

(22) Filed: Mar. 23, 2011

(65) Prior Publication Data

US 2011/0237793 A1 Sep. 29, 2011

Related U.S. Application Data

(60) Provisional application No. 61/316,713, filed on Mar. 23, 2010.

(51) Int. Cl.
*C07D 239/54* (2006.01)
*C07C 311/08* (2006.01)
*C07F 7/08* (2006.01)

(52) U.S. Cl.
CPC ............ *C07C 311/08* (2013.01); *C07D 239/54* (2013.01); *C07F 7/0812* (2013.01)

(58) Field of Classification Search
CPC .... C07D 239/54; C07C 311/06; C07F 7/0812
USPC ........................................................ 544/312
See application file for complete search history.

(56) References Cited

U.S. PATENT DOCUMENTS

| 4,239,888 | A | 12/1980 | Miller |
| 4,588,729 | A | 5/1986 | Teranishi et al. |
| 5,084,084 | A | 1/1992 | Satow et al. |
| 5,127,935 | A | 7/1992 | Satow et al. |
| 5,154,755 | A | 10/1992 | Satow et al. |
| 5,162,326 | A | 11/1992 | Naka et al. |
| 5,164,396 | A | 11/1992 | Grosscurt et al. |
| 6,380,387 | B1 | 4/2002 | Sidduri et al. |
| 6,537,948 | B1 | 3/2003 | Tohyama et al. |
| 6,794,509 | B1 | 9/2004 | Nishigaki et al. |
| 8,178,547 | B2 | 5/2012 | Steiner et al. |
| 8,415,351 | B2 * | 4/2013 | Wagner et al. ............. 514/235.8 |

FOREIGN PATENT DOCUMENTS

| JP | 5213755 A | 8/1993 |
| WO | WO9705117 A1 | 2/1997 |
| WO | WO0142225 A2 | 6/2001 |
| WO | WO0142225 A3 | 6/2001 |
| WO | WO0190121 A2 | 11/2001 |
| WO | WO2005021500 A1 | 3/2005 |
| WO | WO2007138242 A1 | 12/2007 |
| WO | WO2009039127 A1 | 3/2009 |
| WO | WO2009039134 A1 | 3/2009 |
| WO | WO2009039135 A1 | 3/2009 |

OTHER PUBLICATIONS

Mandal et al. J. Org. Chem., 2007, 72 (17), 6599-6601.*
Trost et al. J. Am. Chem. Soc., 2002, 124 (27), pp. 7922-7923. Abstract Provided.*
Ansel H.C., et al., Ansel's Pharmaceutical Dosage forms and Drug Delivery Systems, 8th Edition, Lippincott Williams & Wilkins, 2005, Table of Contents.
Aulton M.E., ed., The Design of Dosage Forms : in Pharmaceutics: The Science of Dosage Form Design, 2nd Edition, Churchill Livingstone, 2004, Table of Contents.
Austin W.B., et al., "Facile Synthesis of Ethynylated Benzoic Acid Derivatives and Aromatic Compounds via Ethynyltrimethylsilane," Journal of Organic Chemistry, 1981, vol. 46 (11), pp. 2280-2286.
Baltrushis R.S., et al., "Bromo Derivatives of 1-(4-hydroxyphenyl)dihydrouracil and—(4-hydroxyphenyl)-5- or -6-Methyldihydrouracils," Chemistry of Heterocyclic Compounds, 1982, vol. 18 (9), pp. 1251-1254.
Blight K.J., et al., "Efficient Initiation of HCV RNA Replication in Cell Culture," 2000, vol. 290 (5498), pp. 1972-1974.
Blight K.J., et al., "Efficient Replication of Hepatitis C Virus Genotype 1 a RNAs in Cell Culture," 2003, vol. 77 (5), pp. 3181-3190.
De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.
Francesco R., et al., "Challenges and Successes in Developing New Therapies for Hepatitis C," 2005, vol. 436 (7053), pp. 953-960.
Gravel M., et al., "Practical Procedure for the Preparation of Functionalized (E)-1-Alkenylboronic Acids Including the Unprecedented 1-Alkoxycarbonyl Derivatives," 2004, vol. 36 (6), pp. 573-579.
Hilfiker R., et al., "Relevance of Solid-state Properties for Pharmaceutical Products," Polymorphism, 2006, pp. 1-19.
International Preliminary Report on Patentability and Written Opinion for Application No. PCT/US2008/076576, mailed on Feb. 12, 2010, 38 pages.
International Preliminary Report on Patentability and Written Opinion for Application No. PCT/US2008/076592, mailed on Mar. 24, 2010, 7 pages.
International Preliminary Report on Patentability and Written Opinion for Application No. PCT/US2008/076594, mailed on Mar. 24, 2010, 7 pages.
International Search Report for Application No. PCT/US2008/076576, mailed on Dec. 22, 2008, 4 pages.
International Search Report for Application No. PCT/US2008/076592, mailed on Feb. 16, 2009, 2 pages.

(Continued)

*Primary Examiner* — Venkataraman Balasubramanian
(74) *Attorney, Agent, or Firm* — Neal, Gerber & Eisenberg LLP; Kevin A. O'Connor

(57) ABSTRACT

This invention is directed to: (a) processes for preparing a compound and salts thereof that, inter alia, are useful for inhibiting hepatitis C virus (HCV); (b) intermediates useful for the preparation of the compound and salts; (c) pharmaceutical compositions comprising the compound or salts; and (d) methods of use of such compositions.

26 Claims, No Drawings

(56) References Cited

OTHER PUBLICATIONS

International Search Report for Application No. PCT/US2008/076594, mailed on Dec. 30, 2008, 2 pages.
International Search Report for Application No. PCT/US2010/028433, mailed on May 31, 2010, 4 pages.
Jacobsen M.F., et al., "Efficient N-Arylation and N-Alkenylation of the Five DNA/RNA Nucleobases," Journal of Organic Chemistry, 2006, vol. 71 (24), pp. 9183-9190.
Koch Uwe et al., "2-(2-thienyl)-5,6-dihydroxy-4-carboxypyrimidines as inhibitors of the hepatitis C virus NS5B polymerase: Discovery, SAR, modeling, and mutagenesis," Journal of Medicinal Chemistry, vol. 49(5), pp. 1693-1705 , 2006.
Lal G.S. et al., "A Convenient Synthesis of 5-Fluoropyrimidines Using 1-(Chloromethyl)-4-fluoro-1,4-diazabicyclo[2.2.2]octane Bis(tetrafluoroborate)-SELECTFLUOR Reagent," J. Org. Chem, vol. 60 (22), pp. 7340-7342, 1995.
Lohmann V., et al., "Replication of Subgenomic Hepatitis C Virus RNAs in a Hepatoma Cell Line," Science, 1999, vol. 285 (5424), pp. 110-113.
Mathe C., et al., "L-nucleoside Enantiomers as Antivirals Drugs: A Mini-review," Antiviral Research, 2006, vol. 71, pp. 276-281.
Micheli F., et al., "Phenylethynyl-Pyrrolo[1,2-a]pyrazine: A New Potent and Selective Tool in the mGluR5 Antagonists Arena," Bioorganic and Medicinal Chemistry Letters, 2008, vol. 18 (6), pp. 1804-1809.
Miller M.W., et al., "Anticoccidial Activity of 1-Phenyluracils," Journal of Medicinal Chemistry, 1983, vol. 26 (7), pp. 1075-1076.
Morrison J.F., et al., "Approaches to the Study and Analysis of the Inhibition of Enzymes by Slow- and Tight-Binding Inhibitors," Comments Molecular Cellular Biophysics, 1985, vol. 2(6), pp. 347-368.
Ohira S., "Methanolysis of Dimethyl (1-Diazo-2-Oxopropyl)Phosphonate: Generation of Dimethyl(DiazoMethyl)Phosphonate and Reaction with Carbonyl Compounds," Synthetic Communications, 1989, vol. 19 (3-4), pp. 561-564.
Onitsuka K., et al., "Living Polymerization of Bulky Aryl Isocyanide with Arylrhodium Complexes," Organometallics, 2006, vol. 25 (5), pp. 1270-1278.
Remington J.P., ed., Pharmaceutical Sciences, 15th Edition, Mack Publishing Company, 1975, pp. 411-415.
Santana L., et al., "A Slightly Shorter Route to Carbocyclic Nucleosides. Synthesis of (±)-trans- I [2-(Hydroxymethyl)cyclopentylmethyl]uracil," Journal of Heterocyclic Chemistry, 1999, vol. 36, pp. 293-295.
Supplementary International Search Report for Application No. PCT/US2008/076576, mailed on Jan. 14, 2010, 2 pages.
Taylor W.P., et al., "Quiescent Affinity Inactivators of Protein Tyrosine Phosphatases," Bioorganic & Medicinal Chemistry, 1996, vol. 4 (9), pp. 1515-1520.
Ueno Y., et al., "Synthesis and Properties of Nucleic Acid Analogues Consisting of a Benzene-Phosphate Backbone," Journal of Organic Chemistry, 2005, vol. 70 (20), pp. 7925-7935.
Zhou T., et al., "Hypervalent Iodine in Synthesis: Part 86. Selective Copper-catalyzed N-monoarylation and N1, N3 Diarylation of Uracil and its Derivatives with Diaryliodonium Salts," Helvetica Chimica Ada, 2005, vol. 88 (2), pp. 290-296.

\* cited by examiner

PROCESS FOR PREPARING ANTIVIRAL COMPOUND

CROSS REFERENCE TO RELATED APPLICATIONS

This patent application claims priority to U.S. Provisional Patent Application No. 61/316,713 which was filed Mar. 23, 2010. The entire text of that application is incorporated by reference into this patent application.

FIELD OF THE INVENTION

This invention is directed to: (a) processes for preparing a compound and salts thereof that, inter alia, are useful for inhibiting hepatitis C virus (HCV); (b) intermediates useful for the preparation of the compound and salts; (c) pharmaceutical compositions comprising the compound or salts; and (d) methods of use of such compositions.

BACKGROUND OF THE INVENTION

Hepatitis C is a blood-borne, infectious, viral disease that is caused by a hepatotropic virus called HCV. At least six different HCV genotypes (with several subtypes within each genotype) are known to date. In North America, HCV genotype 1a predominates, followed by HCV genotypes 1b, 2a, 2b, and 3a. In the United States, HCV genotypes 1, 2, and 3 are the most common, with about 80% of the hepatitis C patients having HCV genotype 1. In Europe, HCV genotype 1b is predominant, followed by HCV genotypes 2a, 2b, 2c, and 3a. HCV genotypes 4 and 5 are found almost exclusively in Africa. As discussed below, the patient's HCV genotype is clinically important in determining the patient's potential response to therapy and the required duration of such therapy.

An HCV infection can cause liver inflammation (hepatitis) that is often asymptomatic, but ensuing chronic hepatitis can result in cirrhosis of the liver (fibrotic scarring of the liver), liver cancer, and/or liver failure. The World Health Organization estimates that about 170 million persons worldwide are chronically infected with HCV, and from about three to about four million persons are newly infected globally each year. According to the Centers for Disease Control and Prevention, about four million people in the United States are infected with HCV. Co-infection with the human immunodeficiency virus (HIV) is common, and rates of HCV infection among HIV positive populations are higher.

There is a small chance of clearing the virus spontaneously, but the majority of patients with chronic hepatitis C will not clear it without treatment. Indications for treatment typically include proven HCV infection and persistent abnormal liver function tests. There are two treatment regimens that are primarily used to treat hepatitis C: monotherapy (using an interferon agent—either a "conventional" or longer-acting pegylated interferon) and combination therapy (using an interferon agent and ribavirin). Interferon, which is injected into the bloodstream, works by bolstering the immune response to HCV; and ribavirin, which is taken orally, is believed to work by preventing HCV replication. Taken alone, ribavirin does not effectively suppress HCV levels, but an interferon/ribavirin combination is more effective than interferon alone. Typically, hepatitis C is treated with a combination of pegylated interferon alpha and ribavirin for a period of 24 or 48 weeks, depending on the HCV genotype.

The goal of treatment is sustained viral response—meaning that HCV is not measurable in the blood after therapy is completed. Following treatment with a combination of pegylated interferon alpha and ribavirin, sustained cure rates (sustained viral response) of about 75% or better occur in people with HCV genotypes 2 and 3 in 24 weeks of treatment, about 50% in those with HCV genotype 1 with 48 weeks of treatment, and about 65% in those with HCV genotype 4 in 48 weeks of treatment.

Treatment may be physically demanding, particularly for those with prior history of drug or alcohol abuse, because both interferon and ribavirin have numerous side effects. Common interferon-associated side effects include flu-like symptoms, extreme fatigue, nausea, loss of appetite, thyroid problems, high blood sugar, hair loss, and skin reactions at the injection site. Possible serious interferon-associated side effects include psychoses (e.g., suicidal behavior), heart problems (e.g., heart attack, low blood pressure), other internal organ damage, blood problems (e.g., blood counts falling dangerously low), and new or worsening autoimmune disease (e.g., rheumatoid arthritis). Ribavirin-associated side effects include anemia, fatigue, irritability, skin rash, nasal stuffiness, sinusitis, and cough. Ribavirin can also cause birth defects, so pregnancy in female patients and female partners of male patients must be avoided during treatment and for six months afterward.

Some patients do not complete treatment because of the serious side effects discussed above; other patients (non-responders) continue to have measurable HCV levels despite treatment; and yet other patients (relapsers) appear to clear the virus during therapy, but the virus returns sometime after completion of the treatment regimen. Thus, there continues to be a need for alternative compositions and methods of treatment (used either in combination with, or in lieu of, an interferon agent and/or ribavirin) to prevent the progression of liver damage from hepatitis C. This invention provides processes for preparing one such compound—(E)-N-(4-(3-tert-butyl-5-(2,4-dioxo-3,4-dihydro-pyrimidin-1(2H)-yl)-2-methoxystyryl)phenyl)methanesulfonamide) (compound I)—and salts thereof.

SUMMARY OF THE INVENTION

This invention is directed to a process for preparing (E)-N-(4-(3-tert-butyl-5-(2,4-dioxo-3,4-dihydropyrimidin-1(2H)-yl)-2-methoxystyryl)phenyl)methanesulfonamide (compound I) or a salt thereof, wherein the process comprises reducing N-(4-((3-tert-butyl-5-(2,4-dioxo-3,4-dihydro pyrimidin-1(2H)-yl)-2-methoxy-phenyl)ethynyl)phenyl)methanesulfonamide (compound 6).

This invention also is directed to compound I and salt thereof prepared by the above process.

This invention also is directed to a process for preparing compound 6.

This invention also is directed to compound 6.

This invention also is directed to various intermediates useful for preparing compound 6 as well as to processes for preparing those intermediates.

This invention also is directed to compositions (including pharmaceutical compositions) that comprise compound I or salt thereof that are prepared by the above processes. Optionally, the compositions can comprise one or more additional therapeutic agents.

This invention also is directed to methods of use of the above compositions to, for example, inhibit replication of a ribonucleic acid (RNA) virus (including HCV) or treat a disease treatable by inhibiting HCV RNA polymerase (including hepatitis C).

Further benefits of Applicants' invention will be apparent to one skilled in the art from reading this patent application.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. Process for Preparing (E)-N-(4-(3-tert-butyl-5-(2, 4-dioxo-3,4-dihydropyrimidin-1(2H)-yl)-2-methoxystyryl)phenyl)methanesulfonamide (compound I)

As discussed above, this invention is directed, in part, to a process for preparing (E)-N-(4-(3-tert-butyl-5-(2,4-dioxo-3, 4-dihydropyrimidin-1(2H)-yl)-2-methoxystyryl)phenyl) methanesulfonamide (compound I) or a salt thereof. The process comprises reducing N-(4-((3-tert-butyl-5-(2,4-dioxo-3, 4-dihydropyrimidin-1(2H)-yl)-2-methoxyphenyl)ethynyl) phenyl)methanesulfonamide (compound 6):

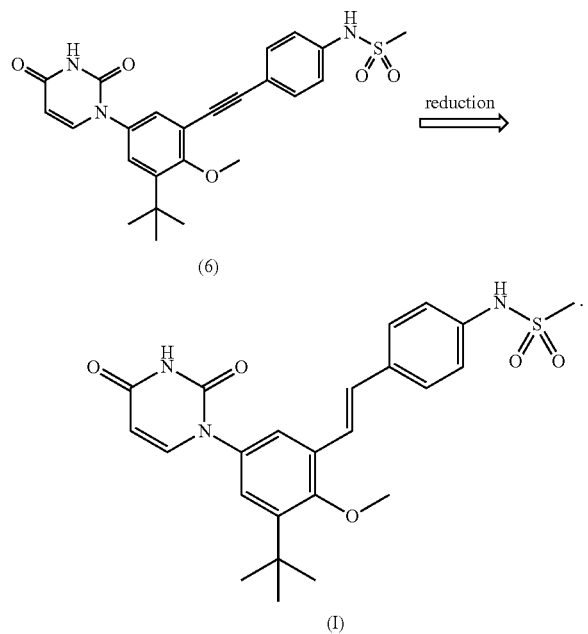

The preparation of starting compound 6 is discussed below. Compound 6 is reduced using a reducing agent.

In some embodiments, the reducing agent is hydrogen source.

In some embodiments, the reducing agent is silane. Suitable silanes include, for example, triethylsilane, phenylsilane, diphenylsilane, tripropylsilane, triphenylsilane, tribenzylsilane, 1,1,1,3,5,5,5-heptamethyltrisiloxane, tributylsilane, di-tert-butylsilane, diethyloxysilane, dimethoxysilane, phenyldiethoxyethylsilane, dimethylsilane, halosilane, and tris(trimethylsilyl)silane. In some embodiments, the silane is triethylsilane. In other embodiments, the silane is phenylsilane. In yet other such embodiments, the silane is diphenylsilane. In yet other embodiments, the silane is tripropylsilane. In yet other embodiments, the silane is triphenylsilane. In yet other embodiments, the silane is tribenzylsilane. In yet other embodiments, the silane is 1,1,1,3,5,5,5-heptamethyltrisiloxane. In further embodiments, the silane is tributylsilane. In yet further embodiments, the silane is di-tert-butylsilane. In yet further embodiments, the silane is diethyloxysilane. In yet further embodiments, the silane is dimethoxysilane. In yet other embodiments, the silane is phenyldiethoxyethylsilane. In yet further embodiments, the silane is dimethylsilane. In yet further embodiments, the silane is halosilane. In yet further embodiments, the silane is tris(trimethylsilyl)silane.

In some embodiments, the reducing agent is disilane. Suitable disilanes include, for example, hexamethyldisilane, hexaphenyldisilane, 1,2-diphenyltetramethyldisilane, 1,2-dimethyl-1,1,2,2-tetra-phenyldisilane, 1,1,2,2-tetramethyldisilane, 1,2-diethoxy-1,1,2,2-tetramethyldisilane, 1,2-dimethoxy-1,1,2,2-tetramethyldisilane, and hexamethoxydisilane. In some embodiments, the disilane is hexame-thyldisilane. In other embodiments, the disilane is hexaphenyldisilane. In yet other embodiments, the disilane is 1,2-diphenyltetramethyldisilane. In yet other embodiments, the disilane is 1,2-dimethyl-1,1,2,2,-tetraphenyldisilane. In further embodiments, the disilane is 1,1,2,2-tetramethyldisilane. In yet further embodiments, the disilane is 1,2-diethoxy-1,1,2,2-tetramethyldisilane. In yet further embodiments, the disilane is 1,2-dimethoxy-1,1,2,2-tetramethyldisilane. In yet further embodiments, the disilane is hexamethoxydisilane.

Compound 6 may be reduced in the presence of catalyst. In some embodiments, the catalyst is transition metal catalyst. In some such embodiments, the catalyst is palladium catalyst. Suitable palladium catalysts include, for example, tetrakis (triphenylphosphine)palladium (0), dichlorobis(tri-o-tolylphosphine)palladium (II), palladium (II) acetate, [1,1'-bis(diphenylphosphino) ferrocene]dichloropalladium (II), tris(dibenzylideneacetone) dipalladium (0), dichloro(dibenzylidene-acetone)dipalladium (II), dichlorotris(cyclohexylphosphine) palladium (II), dichlorobis(triphenyl-phosphine) palladium (II), and chloro(η3-allyl)palladium(II) dimer-triphenylphosphine. In some embodiments, the catalyst is tetrakis(triphenylphosphine) palladium (0). In other embodiments, the catalyst is dichlorobis(tri-o-tolylphosphine) palladium (II). In other embodiments, the catalyst is palladium (II) acetate. In other embodiments, the catalyst is [1,1'-bis(diphenylphosphino)ferrocene]dichloro palladium (II). In yet other embodiments, the catalyst is tris(dibenzylideneacetone) dipalladium (0). In yet other embodiments, the catalyst is dichloro(dibenzylideneacetone) dipalladium (II). In further embodiments, the catalyst is dichlorotris(cyclohexylphosphine) palladium (II). In yet further embodiments, the catalyst is dichlorobis(triphenylphosphine) palladium (II). In yet further embodiments, the catalyst is chloro(η3-allyl)palladium(II) dimer-triphenylphosphine.

In some embodiments, compound 6 is reduced in the presence of solvent. Suitable solvents include, for example, terahydrofuran, dimethylformamide, dimethylacetamide, and N-methyl-pyrrolidone. In some embodiments, the solvent is terahydrofuran. In some such other embodiments, the solvent is dimethylformamide. In yet other such embodiments, the solvent is dimethylacetamide. In yet other such embodiments, the solvent is N-methylpyrrolidone.

In some embodiments, compound 6 is reduced at a temperature of from about 20° C. to about 130° C. In some such embodiments, the temperature is from about 65° C. to about 85° C.

In some embodiments, compound 6 is reduced in inert atmosphere. In some such embodiments, the inert atmosphere is provided by nitrogen. In some other such embodiments, the inert atmosphere is provided by argon.

B. Process for Preparing N-(4-((3-tert-butyl-5-(2,4-dioxo-3,4-dihydropyrimidin-1(2H)-yl)-2-methoxyphenyl)ethynyl)phenyl)methanesulfonamide (compound 6)

In some embodiments, compound 6 is prepared by reacting 1-(3-tert-butyl-5-ethynyl-4-methoxyphenyl)pyrimidine-2,4 (1H,3H)-dione (compound 4) with compound 2 selected from the group consisting of N-(4-iodophenyl)methanesulfonamide (compound 2a), N-(4-bromophenyl)methanesulfonamide (compound 2b), N-(4-chlorophenyl)methanesulfonamide (compound 2c), N-(4-[(arylsulfonyl)oxy] phenyl)methanesulfonamide (compound 2d), and N-(4-[(perfluoroalkylsulfonyl) oxy]phenyl)methanesulfonamide (compound 2e) as follows:

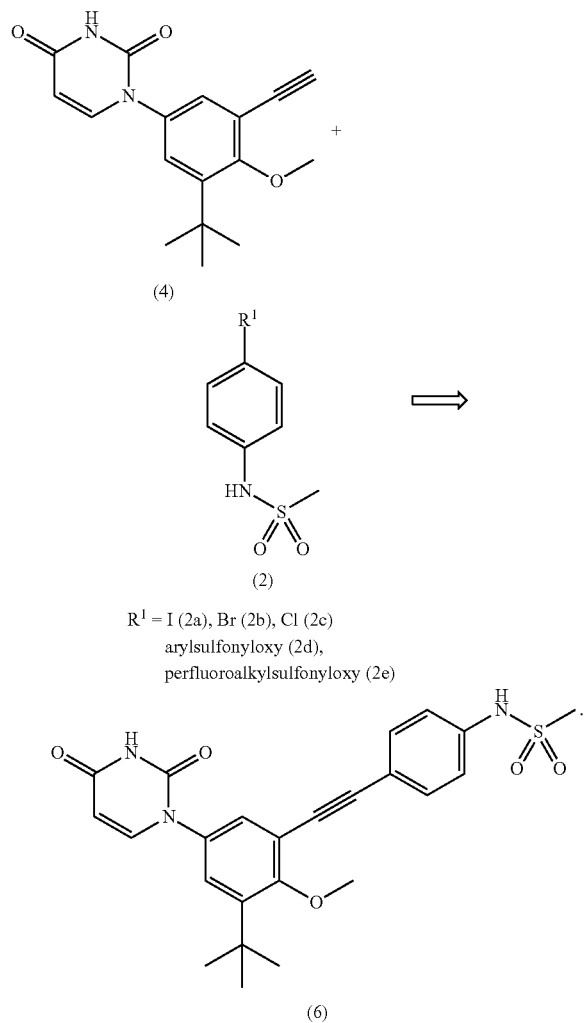

The preparations of starting compound 2 and compound 4 are discussed below.

In some embodiments, compound 4 and compound 2 are reacted in a Sonogashira reaction.

In some embodiments, compound 4 and compound 2 are reacted in the presence of palladium catalyst. Suitable palladium catalyst include, for example, tetrakis(triphenylphosphine)palladium (0), dichlorobis(tri-o-tolylphosphine)palladium (II), palladium (II) acetate, [1,1'-bis(diphenylphosphino) ferrocene]dichloropalladium (II), tris (dibenzylideneacetone) dipalladium (0), dichloro (dibenzylidene acetone)dipalladium (II), and dichlorobis (triphenylphosphine) palladium (II). In some embodiments, the palladium catalyst is tetrakis(triphenylphosphine) palladium (0). In other embodiments, the palladium catalyst is dichlorobis(tri-o-tolylphosphine)palladium (II). In other embodiments, the palladium catalyst is palladium (II) acetate. In yet other embodiments, the palladium catalyst is [1,1'-bis(diphenylphosphino) ferrocene]dichloropalladium (II). In yet other embodiments, the palladium catalyst is tris(dibenzylideneacetone) dipalladium (0). In yet other embodiments, the palladium catalyst is dichloro(dibenzylideneacetone)dipalladium (II). In further embodiments, the palladium catalyst is dichlorobis(triphenylphosphine) palladium (II).

In some embodiments, compound 4 and compound 2 are reacted in the presence of copper catalyst (in addition to palladium catalyst). Suitable copper catalysts include, for example, copper (I) oxide and halide salts of copper (I). Suitable halide salts of copper (I) include, for example, copper (I) iodide, copper (I) bromide, copper (I) iodide dimethyl sulfide, and copper (I) chloride. In some embodiments, the copper catalyst is copper (I) oxide. In other embodiments, the copper catalyst is copper (I) iodide. In other embodiments, the copper catalyst is copper (I) bromide. In yet other embodiments, the copper catalyst is copper (I) iodide dimethyl sulfide. In yet other embodiments, the copper catalyst is copper (I) chloride.

In some embodiments, compound 4 and compound 2 are reacted in the presence of base. Suitable bases include, for example, triethylamine, diisopropylethyl amine, sodium carbonate, cesium carbonate, and potassium carbonate. In some embodiments, the base is triethylamine. In other embodiments, the base is diisopropylethyl amine. In yet other embodiments, the base is sodium carbonate. In yet other embodiments, the base is cesium carbonate. In yet other embodiments, the base is potassium carbonate.

In some embodiments, compound 4 and compound 2 are reacted in the presence of solvent. Suitable solvents include, for example, terahydrofuran, dimethylformamide, dimethoxyethane, dimethylacetamide, N-methylpyrrolidone, and toluene. In some embodiments, the solvent is terahydrofuran. In other embodiments, the solvent is dimethylformamide. In other embodiments, the solvent is dimethoxyethane. In other embodiments, the solvent is dimethylacetamide. In yet other embodiments, the solvent is N-methylpyrrolidone. In yet other embodiments, the solvent is toluene.

In some embodiments, compound 4 and compound 2 are reacted in inert atmosphere. In some such embodiments, the inert atmosphere is provided by nitrogen. In other such embodiments, the inert atmosphere is provided by argon.

In some embodiments, compound 4 and compound 2 are reacted at a temperature of from about 20° C. to about 130° C. In some such embodiments, the temperature is from about 20° C. to about 30° C.

In some embodiments, compound 2 is compound 2a. In other embodiments, compound 2 is compound 2b. In yet other embodiments, compound 2 is compound 2c. In yet other embodiments, compound 2 is compound 2d. In some such embodiments, aryl is phenyl in compound 2d. In some other such embodiments, aryl is naphthyl in compound 2d. In yet other embodiments, compound 2 is compound 2e. In some such embodiments, perfluoroalkyl is perfluoro-$C_1$-$C_6$-alkyl in compound 2e.

In some embodiments, compound 4 and compound 2 are reacted as follows:

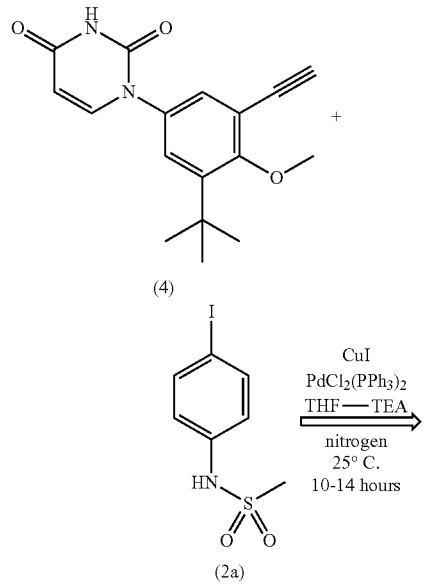

C. N-(4-((3-tert-butyl-5-(2,4-dioxo-3,4-dihydropyrimidin-1(2H)-yl)-2-methoxyphenyl)ethynyl)phenyl)methanesulfonamide (compound 6)

This invention is directed, in part, to N-(4-((3-tert-butyl-5-(2,4-dioxo-3,4-dihydropyrimidin-1(2H)-yl)-2-methoxyphenyl)ethynyl)phenyl)methanesulfonamide (compound 6) or a salt thereof:

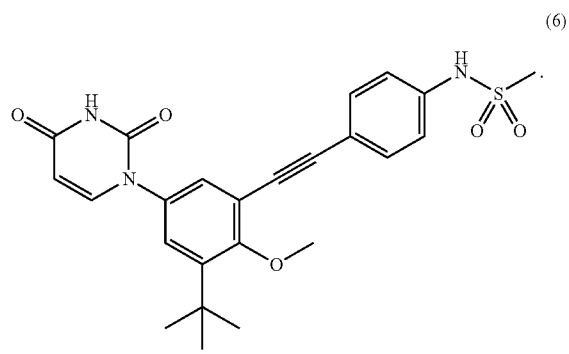 [SMILES: COc1c(C#Cc2ccc(NS(C)(=O)=O)cc2)cc(-n2ccc(=O)[nH]c2=O)cc1C(C)(C)C]

D. Preparation of Compound 2

As discussed above, compound 2 is selected from the group consisting of N-(4-iodophenyl)methanesulfonamide (compound 2a), N-(4-bromophenyl)methanesulfonamide (compound 2b), N-(4-chlorophenyl)methanesulfonamide (compound 2c), N-(4-[(arylsulfonyl)oxy]phenyl)methanesulfonamide (compound 2d), and N-(4-[(perfluoroalkylsulfonyl)oxy]phenyl)methanesulfonamide (compound 2e). It is Applicants' understanding that compound 2 is commercially available. It may also be prepared by one skilled in the art without undue experimentation.

In some embodiments, compound 2 is prepared by reacting methanesulfonyl chloride (MsCl) with compound 1 selected from the group consisting of 4-iodoaniline (compound 1a), 4-bromoaniline (compound 1b), 4-chloroaniline (compound 1c), and 4-hydroxyaniline (compound 1d). In the case of compound 1d, the subsequent formation of compound 2d ($R^1$=arylsulfonyloxy) and compound 2e ($R^1$=perfluoroalkylsulfonyloxy) can be achieved by, for example, sulfonylation of compound 1d with aryl-$SO_2Cl$ or perfluoroalkyl-$SO_2Cl$, respectively:

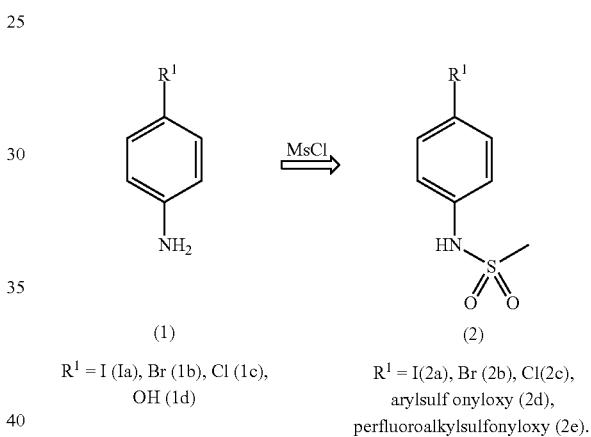

$R^1$ = I (1a), Br (1b), Cl (1c), OH (1d)

$R^1$ = I(2a), Br (2b), Cl(2c), arylsulfonyloxy (2d), perfluoroalkylsulfonyloxy (2e).

It is Applicants' understanding that compound 1 is commercially available. It may also be prepared by one skilled in the art without undue experimentation.

E. Preparation of 1-(3-tert-butyl-5-ethynyl-4-methoxyphenyl)pyrimidine-2,4(1H,3H)-dione (compound 4)

In some embodiments, compound 4 is prepared by reacting ethynyltrimethylsilane

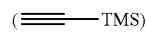

(compound 7) with compound 3 selected from the group consisting of 1-(3-tert-butyl-5-iodo-4-methoxyphenyl)pyrimidine-2,4(1H,3H)-dione (compound 3a), 1-(3-bromo-5-tert-butyl-4-methoxyphenyl)pyrimidine-2,4(1H,3H)-dione (compound 3b), and 1-(3-tert-butyl-5-chloro-4-methoxyphenyl)pyrimidine-2,4(1H,3H)-dione (compound 3c) thus forming 1-(3-tert-butyl-4-methoxy-5-((trimethylsilyl)-ethynyl)phenyl)pyrimidine-2,4(1H,3H)-dione (compound 8):

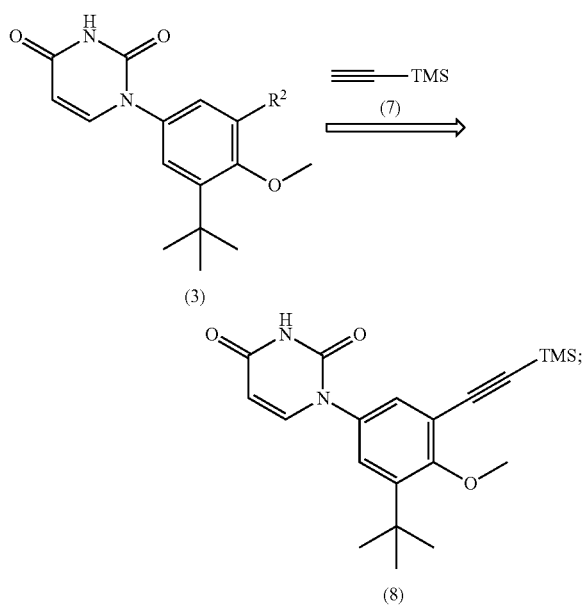

and then
removing the trimethylsilyl (TMS) group from the formed 1-(3-tert-butyl-4-methoxy-5-((trimethylsilyl)ethynyl)phenyl)pyrimidine-2,4(1H,3H)-dione (compound 8):

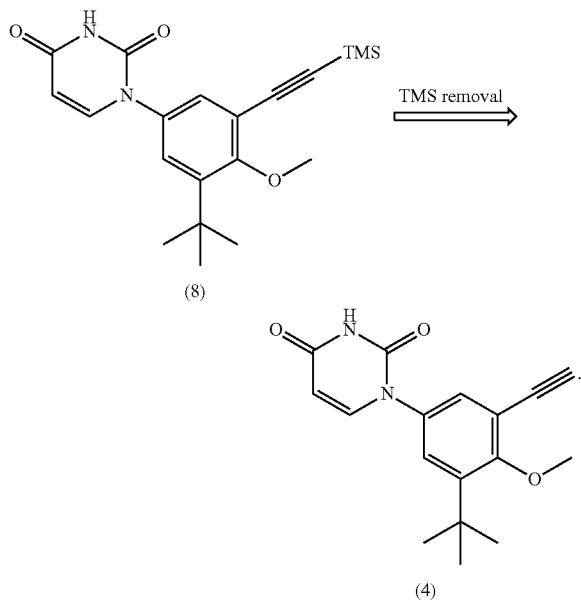

The preparation of compound 3 is discussed below. Compound 7 can be purchased from a commercial source or can be prepared by a person of ordinary skill in the art.

In some embodiments, compound 3 and compound 7 are reacted in the presence of palladium catalyst. Suitable palladium catalyst include, for example, tetrakis(triphenylphosphine)palladium (0), dichlorobis(tri-o-tolylphosphine)palladium (II), palladium (II) acetate, [1,1'-bis(diphenylphosphino) ferrocene]dichloropalladium (II), tris(dibenzylideneacetone) dipalladium (0), dichloro (dibenzylidene-acetone)dipalladium (II), and dichlorobis (triphenylphosphine) palladium (II). In some embodiments, the palladium catalyst is tetrakis(triphenylphosphine) palladium (0). In other embodiments, the palladium catalyst is dichlorobis(tri-o-tolylphosphine)palladium (II). In other embodiments, the palladium catalyst is palladium (II) acetate. In yet other embodiments, the palladium catalyst is [1,1'-bis(diphenylphosphino) ferrocene]dichloropalladium (II). In yet other embodiments, the palladium catalyst is tris(dibenzylideneacetone) dipalladium (0). In yet other embodiments, the palladium catalyst is dichloro(dibenzylideneacetone)dipalladium (II). In further embodiments, the palladium catalyst is dichlorobis(triphenylphosphine) palladium (II).

In some embodiments, compound 3 and compound 7 are reacted in the presence of copper catalyst (in addition to the palladium catalyst). Suitable copper catalysts include, for example, copper (I) oxide and halide salts of copper (I). Suitable halide salts of copper (I) include, for example, copper (I) iodide, copper (I) bromide, copper (I) iodide dimethyl sulfide, and copper (I) chloride. In some embodiments, the copper catalyst is copper (I) oxide. In other embodiments, the copper catalyst is copper (I) iodide. In other embodiments, the copper catalyst is copper (I) bromide. In yet other embodiments, the copper catalyst is copper (I) iodide dimethyl sulfide. In yet other embodiments, the copper catalyst is copper (I) chloride.

In some embodiments, compound 3 and compound 7 are reacted in the presence of base. Suitable bases include, for example, triethylamine, diisopropylethyl amine, sodium carbonate, cesium carbonate, and potassium carbonate. In some embodiments, the base is triethylamine. In other such embodiments, the base is diisopropylethyl amine. In other embodiments, the base is sodium carbonate. In yet other embodiments, the base is cesium carbonate. In further embodiments, the base is potassium carbonate.

In some embodiments, compound 3 and compound 7 are reacted in the presence of solvent. Suitable solvents include, for example, terahydrofuran, dimethylformamide, dimethoxyethane, N-methylpyrrolidone, dimethylacetamide, and toluene. In some embodiments, the solvent is terahydrofuran. In other embodiments, the solvent is dimethylformamide. In yet other embodiments, the solvent is dimethoxyethane. In yet other embodiments, the solvent is N-methylpyrrolidone. In yet other embodiments, the solvent is dimethylacetamide. In further embodiments, the solvent is toluene.

In some embodiments, compound 3 and compound 7 are reacted in inert atmosphere. In some such embodiments, the inert atmosphere is provided by nitrogen. In some other such embodiments, the inert atmosphere is provided by argon.

In some embodiments, compound 3 and compound 7 are reacted at a temperature of from about 20° C. to about 130° C. In some such embodiments, the temperature is from about 20° C. to about 50° C. In other such embodiments, the temperature is from about 20° C. to about 30° C. In yet other such embodiments, the temperature is from about 40° C. to about 50° C.

In some embodiments, compound 3 is compound 3a. In some other embodiments, compound 3 is compound 3b. In yet other embodiments, compound 3 is compound 3c.

In some embodiments, the TMS group is removed by reacting compound 8 with base. Suitable bases, include, for example, tribasic potassium phosphate, potassium carbonate, potassium methoxide, potassium hydroxide, sodium carbonate, and sodium methoxide. In some embodiments, the base is tribasic potassium phosphate. In other embodiments, the base is potassium carbonate. In yet other embodiments, the base is potassium methoxide. In further embodiments, the base is potassium hydroxide. In yet other such embodiments, the base is sodium carbonate. In further embodiments, the base is sodium methoxide.

In some embodiments, the TMS group is removed by reacting compound 8 with fluoride source. Suitable fluoride sources include, for example, potassium fluoride, tetrabutylammonium fluoride, pyridinium fluoride, and triethylammonium fluoride. In some embodiments, the fluoride source is potassium fluoride. In other embodiments, the fluoride source is tetrabutylammonium fluoride. In yet other embodiments, the fluoride source is pyridinium fluoride. In further embodiments, the fluoride source is triethylammonium fluoride.

In some embodiments, TMS group removal is conducted in the presence of solvent. Suitable solvents include, for example, terahydrofuran, dimethylformamide, dimethoxyethane, N-methyl-pyrrolidone, methanol, ethanol, and isopropanol. In some embodiments, the solvent is terahydrofuran. In other embodiments, the solvent is dimethylformamide. In other embodiments, the solvent is dimethoxyethane. In yet other embodiments, the solvent is N-methylpyrrolidone. In yet other embodiments, the solvent is methanol. In yet other embodiments, the solvent is ethanol. In further embodiments, the solvent is isopropanol.

F. 1-(3-tert-butyl-4-methoxy-5-((trimethylsilyl)-ethynyl)phenyl)pyrimidine-2,4(1H,3H)-dione (compound 8)

This invention is directed, in part, to 1-(3-tert-butyl-4-methoxy-5-((trimethylsilyl)ethynyl)phenyl)pyrimidine-2,4(1H,3H)-dione (compound 8) or a salt thereof:

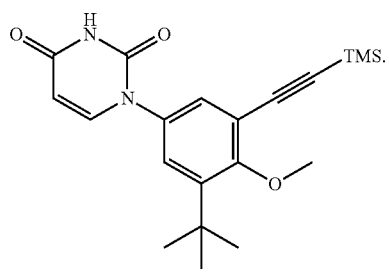

(8)

G. 1-(3-tert-butyl-5-ethynyl-4-methoxyphenyl)pyrimidine-2,4(1H,3H)-dione (compound 4)

This invention is directed, in part, to 1-(3-tert-butyl-5-ethynyl-4-methoxyphenyl)pyrimidine-2,4(1H,3H)-dione (compound 4) or a salt thereof:

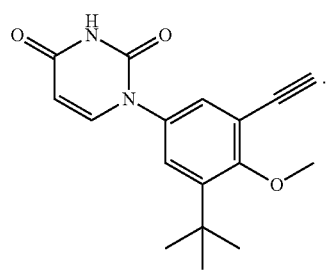

(4)

H. Alternative Process for Preparing N-(4-((3-tert-butyl-5-(2,4-dioxo-3,4-dihydropyrimidin-1(2H)-yl)-2-methoxyphenyl)ethynyl)phenyl)methanesulfonamide (compound 6)

In some embodiments, compound 6 is prepared by reacting N-(4-ethynylphenyl)methane sulfonamide (compound 5) with compound 3 selected from the group consisting of 1-(3-tert-butyl-5-iodo-4-methoxyphenyl)pyrimidine-2,4(1H,3H)-dione (compound 3a), 1-(3-bromo-5-tert-butyl-4-methoxyphenyl)pyrimidine-2,4(1H,3H)-dione (compound 3b), and 1-(3-tert-butyl-5-chloro-4-methoxyphenyl)pyrimidine-2,4(1H,3H)-dione (compound 3c) thus forming N-(4-((3-tert-butyl-5-(2,4-dioxo-3,4-dihydropyrimidin-1(2H)-yl)-2-methoxyphenyl)ethynyl)phenyl)methanesulfonamide (compound 6):

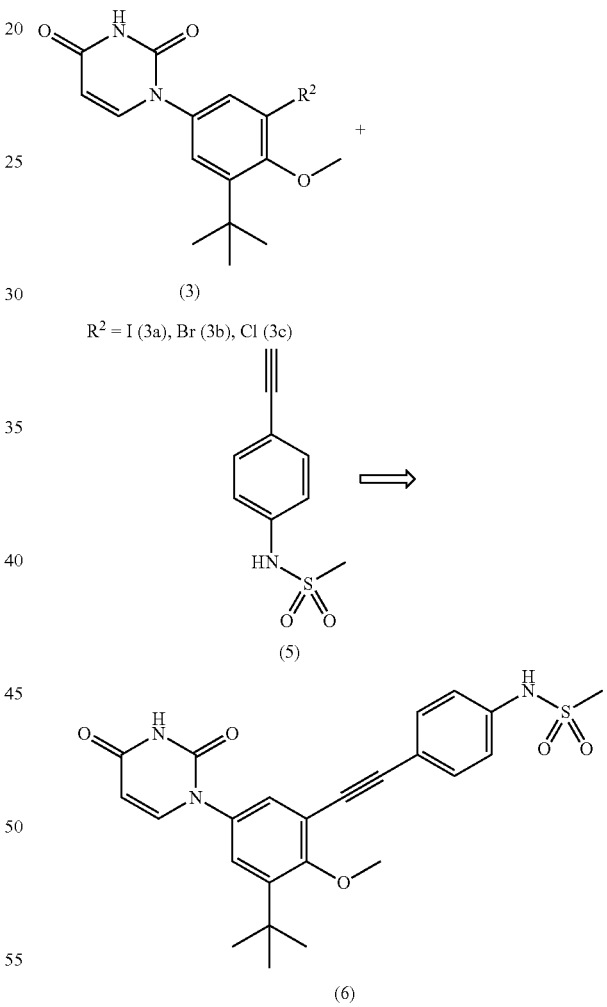

The preparations of compound 3 and compound 5 are discussed below.

In some embodiments, compound 3 and compound 5 are reacted in the presence of palladium catalyst. Suitable palladium catalyst include, for example, tetrakis(triphenylphosphine)palladium (0), dichlorobis(tri-o-tolylphosphine)palladium (II), palladium (II) acetate, [1,1'-bis (diphenylphosphino) ferrocene]dichloropalladium (II), tris (dibenzylideneacetone) dipalladium (0), dichloro (dibenzylidene-acetone)dipalladium (II), and dichlorobis (triphenylphosphine) palladium (II). In some embodiments, the palladium catalyst is tetrakis(triphenylphosphine) palladium (0). In other embodiments, the palladium catalyst is dichlorobis(tri-o-tolylphosphine)palladium (II). In other embodiments, the palladium catalyst is palladium (II) acetate. In yet other such embodiments, the palladium catalyst is [1,1'-bis(diphenylphosphino) ferrocene]dichloropalladium (II). In yet other embodiments, the palladium catalyst is tris(dibenzylideneacetone) dipalladium (0). In yet other embodiments, the palladium catalyst is dichloro(dibenzylideneacetone)dipalladium (II). In further embodiments, the palladium catalyst is dichlorobis(triphenylphosphine) palladium (II).

In some embodiments, compound 3 and compound 5 are reacted in the presence of copper catalyst (in addition to palladium catalyst). Suitable copper catalysts include, for example, copper (I) oxide and halide salts of copper (I). Suitable halide salts of copper (I) include, for example, copper (I) iodide, copper (I) bromide, copper (I) iodide dimethyl sulfide, and copper (I) chloride. In some embodiments, the copper catalyst is copper (I) oxide. In other embodiments, the copper catalyst is copper (I) iodide. In other embodiments, the copper catalyst is copper (I) bromide. In yet other embodiments, the copper catalyst is copper (I) iodide dimethyl sulfide. In yet other embodiments, the copper catalyst is copper (I) chloride.

In some embodiments, compound 3 and compound 5 are reacted in the presence of base. Suitable bases include, for example, triethylamine, diisopropylethyl amine, sodium carbonate, cesium carbonate, and potassium carbonate. In some embodiments, the base is triethylamine. In other embodiments, the base is diisopropylethyl amine. In yet other embodiments, the base is sodium carbonate. In yet other embodiments, the base is cesium carbonate. In further embodiments, the base is potassium carbonate.

In some embodiments, compound 3 and compound 5 are reacted in the presence of solvent. Suitable solvents include, for example, terahydrofuran, dimethylformamide, dimethoxyethane, N-methylpyrrolidone, dimethylacetamide, and toluene. In some embodiments, the solvent is terahydrofuran. In other embodiments, the solvent is dimethylformamide. In yet other embodiments, the solvent is dimethoxyethane. In yet other embodiments, the solvent is N-methylpyrrolidone. In yet other embodiments, the solvent is dimethylacetamide. In further embodiments, the solvent is toluene.

In some embodiments, compound 3 and compound 5 are reacted in inert atmosphere. In some such embodiments, the inert atmosphere is provided by nitrogen. In some other such embodiments, the inert atmosphere is provided by argon.

In some embodiments, compound 3 is compound 3a. In some other embodiments, compound 3 is compound 3b. In yet other embodiments, compound 3 is compound 3c.

I. Preparation of Compound 3

The preparation of compound 3 is described in Example 1 below as well as in International Patent Publication No. WO 2009/039127 which is incorporated herein by reference.

J. Preparation of N-(4-ethynylphenyl)methanesulfonamide (compound 5)

In some embodiments, N-(4-ethynylphenyl)methanesulfonamide (compound 5) is prepared by reacting ethynyltrimethylsilane (≡—TMS)

(compound 7) with compound 2 thus forming N-(4-((trimethylsilyl)ethynyl)phenyl)methanesulfonamide (compound 9):

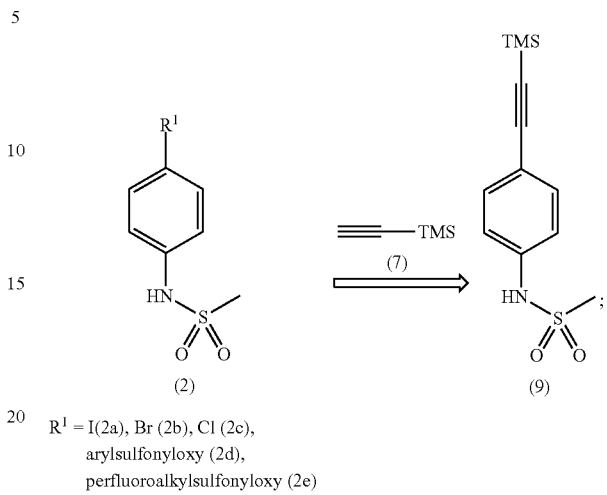

$R^1$ = I(2a), Br (2b), Cl (2c),
arylsulfonyloxy (2d),
perfluoroalkylsulfonyloxy (2e)

and then removing the trimethylsilyl (TMS) group from the formed N-(4-((trimethylsilyl)ethynyl)phenyl)methanesulfonamide (compound 9):

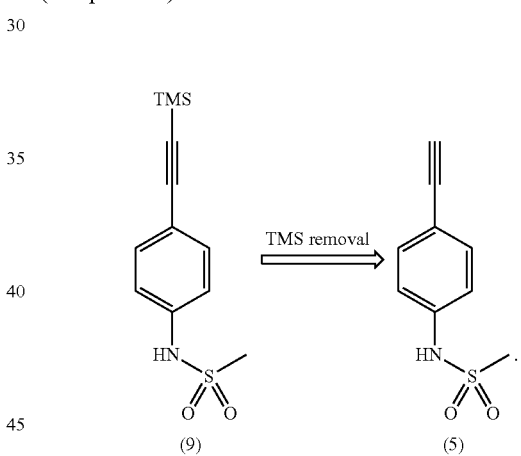

The preparation of compound 2 is discussed above. Compound 7 is commercially available, or, alternatively, can be prepared by a person of ordinary skill in the art.

In some embodiments, compound 2 and compound 7 are reacted in the presence of palladium catalyst. Suitable palladium catalysts include, for example, tetrakis(triphenylphosphine)palladium (0), dichlorobis(tri-o-tolylphosphine)palladium (II), palladium (II) acetate, [1,1'-bis(diphenylphosphino) ferrocene]dichloropalladium (II), tris(dibenzylideneacetone) dipalladium (0), dichloro(dibenzylidene-acetone)dipalladium (II), and dichlorobis(triphenylphosphine) palladium (II). In some embodiments, the palladium catalyst is tetrakis(triphenylphosphine) palladium (0). In other embodiments, the palladium catalyst is dichlorobis(tri-o-tolylphosphine)palladium (II). In yet other embodiments, the palladium catalyst is palladium (II) acetate. In yet other embodiments, the palladium catalyst is [1,1'-bis (diphenylphosphino) ferrocene]dichloropalladium (II). In yet other embodiments, the palladium catalyst is tris(dibenzylideneacetone) dipalladium (0). In yet other embodiments, the palladium catalyst is dichloro(dibenzylideneacetone)dipalladium (II). In yet other embodiments, the palladium catalyst is dichlorobis(triphenylphosphine) palladium (II).

In some embodiments, compound 2 and compound 7 are reacted in the presence of copper catalyst (in addition to palladium catalyst). Suitable copper catalysts include, for example, copper (I) oxide and halide salts of copper (I). Suitable halide salts of copper (I) include, for example, copper (I) iodide, copper (I) bromide, copper (I) iodide dimethyl sulfide, and copper (I) chloride. In some embodiments, the copper catalyst is copper (I) oxide. In other embodiments, the copper catalyst is copper (I) iodide. In other embodiments, the copper catalyst is copper (I) bromide. In yet other embodiments, the copper catalyst is copper (I) iodide dimethyl sulfide. In yet other embodiments, the copper catalyst is copper (I) chloride.

In some embodiments, compound 2 and compound 7 are reacted in the presence of base. Suitable bases include, for example, triethylamine, diisopropylethyl amine, sodium carbonate, cesium carbonate, and potassium carbonate. In some embodiments, the base is triethylamine. In other embodiments, the base is diisopropylethyl amine. In yet other embodiments, the base is sodium carbonate. In yet other embodiments, the base is cesium carbonate. In yet other embodiments, the base is potassium carbonate.

In some embodiments, compound 2 and compound 7 are reacted in the presence of solvent. Suitable solvents include, for example, terahydrofuran, dimethylformamide, dimethoxyethane, N-methylpyrrolidone, dimethylacetamide, and toluene. In some embodiments, the solvent is terahydrofuran. In other embodiments, the solvent is dimethylformamide. In yet other embodiments, the solvent is dimethoxyethane. In yet other embodiments, the solvent is N-methylpyrrolidone. In yet other embodiments, the solvent is dimethylacetamide. In further embodiments, the solvent is toluene.

In some embodiments, compound 2 and compound 7 are reacted in inert atmosphere. In some such embodiments, the inert atmosphere is provided by nitrogen. In some other such embodiments, the inert atmosphere is provided by argon.

In some embodiments, compound 2 and compound 7 are reacted at a temperature of from about 20° C. to about 130° C. In some such embodiments, the temperature is from about 20° C. to about 50° C. In some other such embodiments, the temperature is from about 20° C. to about 30° C. In yet other such embodiments, the temperature is from about 40° C. to about 50° C.

In some embodiments, compound 2 is compound 2a. In some other embodiments, compound 2 is compound 2b. In yet other embodiments, compound 2 is compound 2c. In yet other embodiments, compound 2 is compound 2d. In some such embodiments, aryl is phenyl in compound 2d. In some other such embodiments, aryl is naphthyl in compound 2d. In yet other embodiments, compound 2 is compound 2e. In some such embodiments, perfluoroalkyl is perfluoro-$C_1$-$C_6$-alkyl in compound 2e.

In some embodiments, the TMS group is removed by reacting compound 9 with base. Suitable bases, include, for example, tribasic potassium phosphate, potassium carbonate, potassium methoxide, potassium hydroxide, sodium carbonate, and sodium methoxide. In some embodiments, the base is tribasic potassium phosphate. In other embodiments, the base is potassium carbonate. In yet other embodiments, the base is potassium methoxide. In further embodiments, the base is potassium hydroxide. In yet other such embodiments, the base is sodium carbonate. In further embodiments, the base is sodium methoxide.

In some embodiments, the TMS group is removed by reacting compound 9 with fluoride source. Suitable fluoride sources include, for example, potassium fluoride, tetrabutylammonium fluoride, pyridinium fluoride, and triethylammonium fluoride. In some embodiments, the fluoride source is potassium fluoride. In other embodiments, the fluoride source is tetrabutylammonium fluoride. In yet other embodiments, the fluoride source is pyridinium fluoride. In further embodiments, the fluoride source is triethylammonium fluoride.

In some embodiments, TMS group removal is conducted in the presence of solvent. Suitable solvents include, for example, terahydrofuran, dimethylformamide, dimethoxyethane, N-methyl-pyrrolidone, methanol, ethanol, and isopropanol. In some embodiments, the solvent is terahydrofuran. In other embodiments, the solvent is dimethylformamide. In other embodiments, the solvent is dimethoxyethane. In yet other embodiments, the solvent is N-methylpyrrolidone. In yet other embodiments, the solvent is methanol. In yet other embodiments, the solvent is ethanol. In further embodiments, the solvent is isopropanol.

K. N-(4-ethynylphenyl)methanesulfonamide (compound 5)

This invention also is directed, in part, to N-(4-ethynylphenyl)methanesulfonamide (compound 5) or a salt thereof:

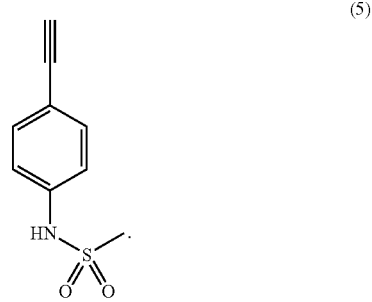

(5)

L. Compositions (E)-N-(4-(3-tert-butyl-5-(2,4-dioxo-3,4-dihydropyrimidin-1(2H)-yl)-2-methoxystyryl)phenyl)methanesulfonamide (compound I) and its salts prepared by the above processes can be used to prepare compositions. These compositions may also comprise one or more conventional pharmaceutically acceptable carriers, adjuvants, and/or vehicles (together referred to as "excipients").

Compositions may be for oral administration in solid dosage form. Such solid dosage forms include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

The total daily dose of a compound or salt (administered in single or divided doses) may be from about 0.001 to about 100 mg/kg, or from about 0.001 to about 30 mg/kg, or from about 0.01 to about 10 mg/kg (i.e., mg of the compound or salt per kg body weight). For example, compound I may be administered in doses of from about 0.5 mg/kg to about 15 mg/kg or from about 1 mg/kg to about 10 mg/kg. Compound I may be administered in a total daily dose amount of from about 50 mg to about 1000 mg or from about 100 mg to about 600 mg or from about 80 mg to about 320 mg. Dosage unit compositions can contain such amounts or submultiples thereof to make up the daily dose. In many instances, the administration of the compound or salt will be repeated a plurality of times. Multiple doses per day may be used to increase the total daily dose, if desired.

Factors affecting the dosage regimen include the type, age, weight, sex, diet, and condition of the patient; the severity of the pathological condition; the severity of the pathological condition; pharmacological considerations, such as the activity, efficacy, pharmacokinetic, and toxicology profiles of the particular compound or salt used; whether a drug delivery system is utilized; and the specific drug combination. Thus, the dosage regimen actually employed can vary widely, and therefore, can derive from the dosage regimen set forth above.

M. Methods of Use

This invention also is directed, in part, to a method for inhibiting replication of an RNA virus. The method comprises exposing the virus to a composition of the invention. In some embodiments, replication of the RNA virus is inhibited in vitro. Typically, replication of the RNA virus is inhibited in vivo. In some embodiments, the RNA virus whose replication is being inhibited is a single-stranded, positive sense RNA virus. In some such embodiments, the RNA virus whose replication is being inhibited is a virus from the Flaviviridae family. In some such embodiments, the RNA virus whose replication is being inhibited is HCV.

This invention also is directed, in part, to a method for inhibiting HCV RNA polymerase. The method comprises exposing the polymerase with a compound, salt, and/or composition of the invention. In some embodiments, HCV RNA polymerase activity is inhibited in vitro. Typically, HCV RNA polymerase activity is inhibited in vivo.

The term "inhibiting" means reducing the level of RNA virus replication/HCV polymerase activity either in vitro or in vivo. For example, if a composition of the invention reduces the level of RNA virus replication by at least about 10% compared to the level of RNA virus replication before the virus was exposed to the composition, then the composition inhibits RNA virus replication. In some embodiments, the composition can inhibit RNA virus replication by at least about 20%, at least about 30%, at least about 40%, at least about 50%, at least about 60%, at least about 70%, at least about 80%, at least about 90%, or at least about 95%.

This invention also is directed, in part, to a method for treating a disease that can be treated by inhibiting HCV RNA polymerase. Thus, this invention also is directed, in part, to a method for treating hepatitis C in an animal in need of such treatment. These methods comprise administering to the animal a compound, salt, and/or composition of the invention. In some embodiments, a therapeutically effective amount of the compound (or salt thereof) is administered to the animal. "Treating" means ameliorating, suppressing, eradicating, preventing, reducing the risk of, and/or delaying the onset of the disease being treated. Applicants specifically intend that the term "treating" encompass administration of the compositions of the invention to an HCV-negative patient that is a candidate for an organ transplant. The methods of treatment are particularly suitable for use with humans, but may be used with other animals, particularly mammals. A "therapeutically-effective amount" or "effective amount" is an amount that will achieve the goal of treating the targeted condition.

In some embodiments, the methods comprise combination therapy, wherein a compound, salt, and/or composition of the invention is co-administered with one or more additional therapeutic agents, such as, for example, another therapeutic agent used to treat hepatitis C (e.g., interferon or interferon/ribavirin combination, or an HCV inhibitor such as, for example, an HCV polymerase inhibitor or an HCV protease inhibitor). The compound, salts, and/or compositions of this invention can also be co-administered with therapeutic agents other than therapeutic agents used to treat hepatitis C (e.g., anti-HIV agents). In these co-administration embodiments, the compound, salts, and/or compositions of the invention and the additional therapeutic agent(s) may be administered in a substantially simultaneous manner (e.g., or within about 5 min of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient.

This invention also is directed, in part, to a use of the compound, salts, and/or compositions of the invention, and, optionally one or more additional therapeutic agents to prepare a medicament.

In some embodiments, the medicament is for co-administration with one or more additional therapeutic agents.

In some embodiments, the medicament is for inhibiting replication of an RNA virus.

In some embodiments, the medicament is for treating hepatitis C.

This invention also is directed, in part, to one or more compositions of the invention, and, optionally one or more additional therapeutic agents, for use as a medicament. In some embodiments, the medicament is for inhibiting replication of an RNA virus. In other embodiments, the medicament is for treating hepatitis C.

EXAMPLES

The following examples are merely illustrative, and not limiting to this disclosure in any way.

Example 1

Preparation of 1-(3-tert-Butyl-5-iodo-4-methoxyphenyl)pyrimidine-2,4(1H,3H)-dione Part A. Preparation of 2-tert-butyl-4,6-diiodophenol 2-tert-Butylphenol (99.95 g, 665.36 mmol) was dissolved in 1250 mL methanol and converted to the corresponding phenoxide with 31.96 g (799.0 mmol, 1.2 equiv.) of sodium hydroxide by stirring the sodium hydroxide pellets at room temperature, and then cooling the reaction mixture in an ice/salt bath. Sodium iodide (299.34 g, 1997.07 mmol, 3.0 equiv.) and 8.3% bleach (1265.83 g, 1411.39 mmol, 2.1 equiv.) were added to the cold reaction solution in four equal portions, the bleach being added while keeping the reaction mixture at <0° C. 500 mL of 20% (w/w) sodium thiosulfate solution was added over an 18-minute period, with the temperature rising from −0.6° C. to 2.5° C. The pH of the reaction mixture was adjusted to approximately 3 by adding 197.5 mL of conc. HCl over a period of 97 min with the reaction temperature going from 1.2° C. to 4.1° C. The resulting slurry was filtered, and the wet cake washed with ~2 L of water. The wet cake was left on the Buchner funnel under vacuum overnight (approximately 15 h) to yield 289.33 g (potency adjusted yield=254.61 g) of the title product.

Part B. Preparation of 1-tert-butyl-3,5-diiodo-2-methoxybenzene

The product from Part A (93% assay, 21.6 g, 50 mmol) was dissolved in 140 mL of acetone. Methyl iodide (4.2 mL, 67.5 mmol, 1.35 equiv.) was added, followed by 50% aqueous sodium hydroxide (5.0 g, 62.5 mmol, 1.25 equiv.). The reaction was stirred overnight, then concentrated to approximately 50-60 mL. 80 mL of heptanes was added followed by 50 mL of water, and the layers were shaken and separated, and the aqueous layer was back extracted with 20 mL of heptanes. The organic layers were combined and washed twice with 50 mL each of 10% aqueous NaCl to afford 91.1 grams of a heptane solution, which assayed to 19.1 g of the title compound.

Part C. Preparation of 1-(3-tert-Butyl-5-iodo-4-methoxyphenyl)pyrimidine-2,4(1H,3H)-dione Uracil (33.3 g, 297 mmol, 1.2 equiv.), $K_3PO_4$ (106 g, 500 mmol, 2.1 equiv.), CuI (4.6 g, 24.2 mmol, 0.1 equiv.), and N-(2-cyanophenyl)picolinamide (6.4 g, 28.7 mmol, 0.12 equiv.) were charged to a flask and inerted with argon. The 1-tert-butyl-3,5-diiodo-2-methoxybenzene was solvent switched into MeCN, dissolved in 1 L DMSO and sparged with argon and added to the solids. The reaction was heated to 60° C. for 16 h. After cooling, the reaction was diluted with 2 L EtOAc and washed with 2.6 L water (back extracted with 3×1 L EtOAc). The combined organic layers were washed with 2×1 L of 0.25M $(CuOAc)_2$ then 2×830 mL 15% $NH_4Cl$ then 800 mL brine. The organic layer was then concentrated and chased with 1 L heptane, then triturated with refluxing 85:15 (v/v) heptane:iPrOAc for 4 h. After cooling, the product was collected by filtration and washed with an additional 330 mL of 85:15 v/v heptanes:EtOAc to yield after drying 66.9 g (70% yield) of the product as a white solid.

Example 2

Preparation of 1-(3-tert-butyl-4-methoxy-5-((trimethylsilyl)-ethynyl)phenyl)pyrimidine-2,4(1H,3H)-dione

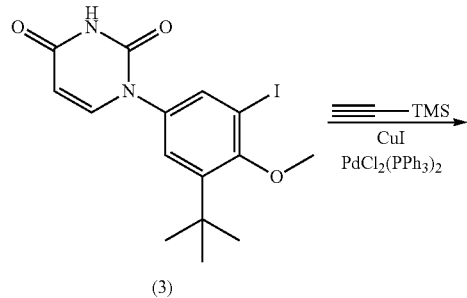

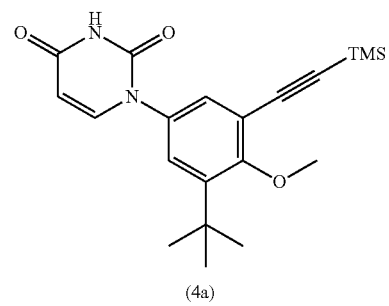

To a flask with condenser, was successively charged 1-(3-tert-butyl-5-iodo-4-methoxyphenyl)pyrimidine-2,4(1H, 3H)-dione (3) (30 g; 75 mmol), copper(I) iodide (0.086 g; 0.450 mmol) and bis(triphenylphosphine)palladium(II) chloride (0.158 g; 0.225 mmol) then charge a solution previously purged with nitrogen of tetrahydrofuran (60 ml) and triethylamine (55.4 ml; 397 mmol). The mixture was stirred at 25° C. for 15 minutes. To the solution was added dropwise ethynyltrimethylsilane (8.83 g; 90 mmol) and the solution mixed at 25° C. for 15 minutes before adjusting the temperature to 45° C. for 18.5 hours. The reaction mixture cooled to ambient and diluted with ethyl acetate (230 mL). The reaction mixture was washed twice with 1% l-Cysteine/5% bicarbonate solution followed by 5% sodium bicarbonate and then a 15% sodium chloride solution. The organic layer was treated with activated carbon and concentrated under reduced pressure. The residual ethyl acetate was chased by charging heptane and concentrating under reduced pressure to an appropriate volume. The heptane slurry was heated at reflux for 2 hours then cooled to 25° C. for 12 hours. The solids were filtered and washed with heptane and dried by vacuum filtration to give 25 grams of the titled compound 4a. $^1$H NMR (400 MHz, $CDCl_3$) δ 8.8 (s, 1H), 7.34-7.27 (m, 2H), 7.21 (d, J=2.8, 1H), 5.83 (d, J=7.9, 1H), 4.13 (s, 3H), 1.41 (s, 9H), 0.29 (s, 9H). MS (APCI) m/z 371.2 (M+H)+.

Example 3

Preparation of 1-(3-tert-butyl-5-ethynyl-4-methoxyphenyl)pyrimidine-2,4(1H,3H)-dione

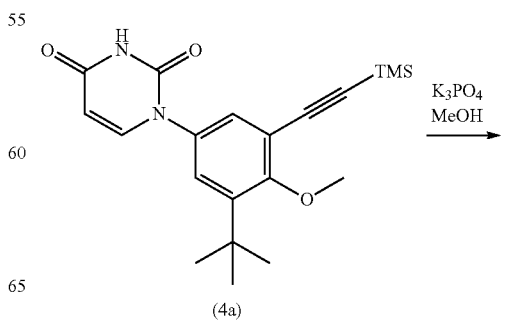

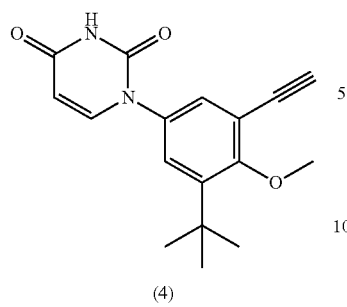

(4)

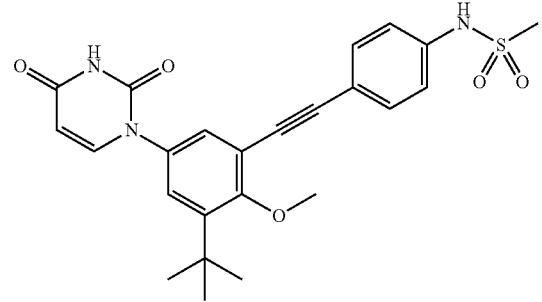

(6)

To a vessel was charged Example 4a (11 g; 29.7 mmol) and Methanol (60 ml). To the mixture was added a 19% potassium phosphate tribasic aqueous solution (30 ml) then the temperature was adjusted at 45° C. and mixed for 3 hours. The reaction temperature was cooled at 35° C. and a 13% acetic acid solution (69 ml) was added to the mixture drop-wise. The slurry was mixed at 55° C. for 90 minutes cooled to 25° C., and stirred for 12 hours. The solids were filtered, washed with water, and dried to give 8.78 grams titled compound 4. $^1$H NMR (400 MHz, CDCl$_3$) δ 8.77 (bs, 1H), 7.30 (d, J=2.7, 1H), 7.27 (d, J=7.9), 7.21 (d, J=2.7, 1H), 5.80 (d, J=7.9, 1H), 4.09 (s, 3H), 3.41 (s, 1H), 1.38 (s, 9H). MS (APCI) m/z 299.2 (M+H)+.

To a flask was added 1-(3-tert-butyl-5-ethynyl-4-methoxyphenyl)pyrimidine-2,4(1H,3H)-dione (4) (6.0 g; 20.11 mmol) and N-(4-iodophenyl)methanesulfonamide (2) (6.0 g; 20.11 mmol). To this was added bis(triphenylphosphine)palladium(II) chloride (0.141 g; 0.201 mmol) and copper (I) chloride (0.077 g; 0.402 mmol). To this was charged a solution tetrahydrofuran (60 ml) and triethylamine (17.8 ml; 121 mmol) previously purged with nitrogen. The reaction was stirred overnight at 25° C.

Isolation of the solids: The reaction mixture was solvent exchanged into methanol and the resulting slurry filtered. The solids were washed with methanol and then reslurried in approximately 7.5 mL methanol per gram solid. This was heated to reflux, cooled to ambient, filtered, and washed with methanol to give the title compound 6. $^1$H NMR (400 MHz, DMSO) δ 11.40 (bs, 1H), 10.08 (bs, 1H), 7.71 (d, J=7.8, 1H), 7.57-7.51 (m, 2H), 7.45 (d, J=2.6, 1H), 7.31-7.21 (m, 3H), 5.63 (d, J=7.8, 1H), 4.08 (s, 3H), 3.05 (s, 3H), 1.35 (s, 9H). MS (APCI) m/z 468.2 (M+H)+$^-$

Example 4

Preparation of N-(4-((3-tert-butyl-5-(2,4-dioxo-3,4-dihydropyrimidin-1(2H)-yl)-2-methoxyphenyl)ethynyl)phenyl)methanesulfonamide

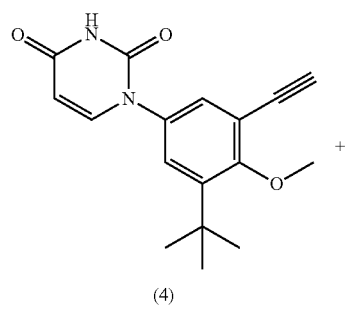

(4)

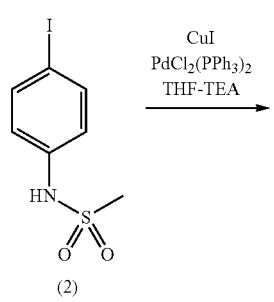

(2)

Example 5

Preparation of (E)-N-(4-(3-tert-butyl-5-(2,4-dioxo-3,4-dihydropyrimidin-1(2H)-yl)-2-methoxystyryl)phenyl)methanesulfonamide

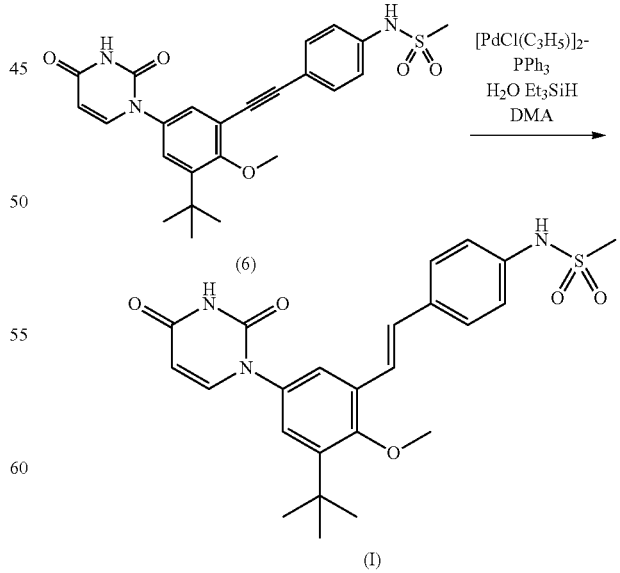

To a flask was successively added N-(4-((3-tert-butyl-5-(2, 4-dioxo-3,4-dihydropyrimidin-1(2H)-yl)-2-methoxyphenyl)

ethynyl)phenyl)methanesulfonamide (6) (20 g; 42.60 mmol); allylpalladium(II) chloride (0.39 g; 1.06 mmol); triphenylphosphine (1.12 g; 4.26 mmol) and a solution of dimethylacetamide (80 ml)/water (2.3 ml) previously purge with nitrogen. The solution was heated at 70° C. for 30 minutes. To the reaction mixture was then added over 3 hours triethylsilane (7.42 g; 63.90 mmol). The mixture was stirred for 12 hours at 70° C. The reaction was cooled at 23° C. then diluted with tetrahydrofuran (180 ml) and successively washed with a solution of 1% Cysteine/2.5% NaHCO$_3$/7% NaCl and a solution of 2.5% NaHCO$_3$/7% NaCl. The organic layer was treated with activated carbon and the filtrate was concentrated down and solvent switched to methanol. The slurry was mixed at 62° C. for 60 minutes, cooled down to 25° C., mixed for 2 hours, filtered, and washed with methanol to give the titled compound. $^1$H NMR (400 MHz, DMSO-D6) δ ppm 1.35 (s, 9 H) 2.99 (s, 3 H) 3.76 (s, 3 H) 5.62 (d, J=7.82 Hz, 1 H) 7.12-7.29 (m, 5 H) 7.51-7.65 (m, 3 H) 7.72 (d, J=7.82 Hz, 1 H) 9.83 (s, 1 H) 11.39 (s, 1 H) MS (APCI) m/z 470.1 (M+H)+.

then added to the reaction mixture. The mixture was heated to 81° C. for total of 18 hours. The reaction mixture was cooled to ambient temperature and quenched with 500 ml THF and 500 ml of a solution of 7% NaCl, 2.5% NaHCO$_3$ and 1% of cysteine. The quenched mixture was stirred for 1 hour and filtered to remove particulates. The filtrate was separated. The aqueous layer was back extracted with 250 mL THF and the combined organic layers washed again with 250 ml of a solution of solution of 7% NaCl, 2.5% NaHCO$_3$ and 1% of cysteine. The organics were treated with activated carbon and the filtrate concentrated and solvent switched to 500 ml of methanol. The slurry was mixed at 50° C. for 60 minutes, cooled to ambient overnight. The slurry was filtered, and the solids washed with methanol, and dried to give 43.86 grams of the titled compound. $^1$H NMR (400 MHz, DMSO-D6) δ ppm 1.35 (s, 9 H) 2.99 (s, 3 H) 3.76 (s, 3 H) 5.62 (d, J=7.82 Hz, 1 H) 7.12-7.29 (m, 5 H) 7.51-7.65 (m, 3 H) 7.72 (d, J=7.82 Hz, 1 H) 9.83 (s, 1 H) 11.39 (s, 1 H) MS (APCI) m/z 470.1 (M+H)+.

Example 6

Preparation of (E)-N-(4-(3-tert-butyl-5-(2,4-dioxo-3,4-dihydropyrimidin-1(2H)-yl)-2-methoxystyryl)phenyl)methanesulfonamide Example 7

Preparation of (E)-N-(4-(3-tert-butyl-5-(2,4-dioxo-3,4-dihydropyrimidin-1(2H)-yl)-2-methoxystyryl)phenyl)methanesulfonamide

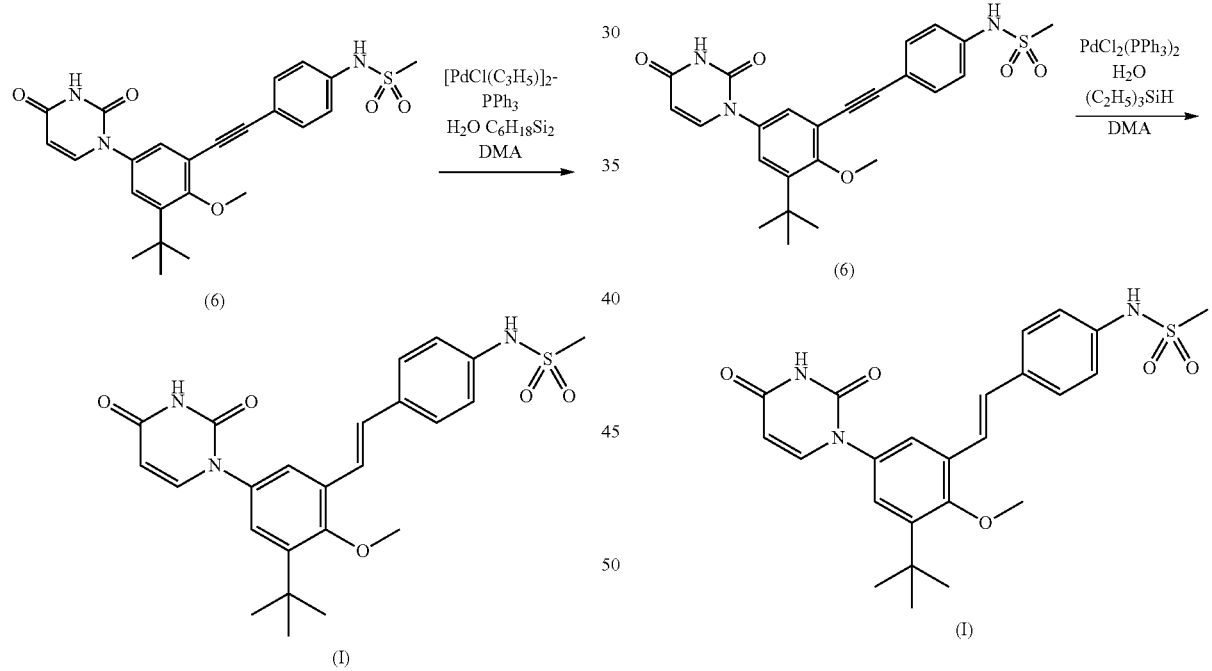

To a flask was added allylpalladium(II) chloride (0.98 g; 2.67 mmol) and triphenyl phosphine (2.8 g; 10.69 mmol). Vacuum and nitrogen purged. Sparged dimethylacetamide (50 ml) (nitrogen bubbled) was added and the solution was mixed at room temperature for 2 hrs. N-(4-((3-tert-butyl-5-(2,4-dioxo-3,4-dihydropyrimidin-1(2 H)-yl)-2-methoxyphenyl)ethynyl)phenyl)methanesulfonamide (6) (50 g; 107 mmol) was dissolved in 100 mL of nitrogen sparged dimethylacetamide in a separate flask. This was inerted with nitrogen after the dissolution. The catalyst solution was transferred to the second flask containing substrate (6). Water (5 ml) and 1,1,1,2,2,2-hexamethyldisilane (16.1 mL; 160 mmol) were To a vessel N-(4-((3-tert-butyl-5-(2,4-dioxo-3,4-dihydropyrimidin-1(2H)-yl)-2-methoxyphenyl)ethynyl)phenyl) methanesulfonamide (6) (5.00 g; 10.69 mmol) and bis(triphenylphosphine)palladium(II) chloride (0.375 g; 5.35 mmol) are charged and the vessel is purged with nitrogen. Nitrogen purged dimethylacetamide (20 ml) and water (0.578 g, 32.1 mmol) are charged to the vessel and the mixture was heated to 70° C. Triethylsilane (2.49 g, 21.4 mmol) was charged over 2 hours at a temperature of 70° C. The mixture was heated at 70° C. for approximately 5 hours and cooled to ambient temperature. The mixture was diluted with tetrahydrofuran (40 g) and extracted with a 1% Cysteine/2.5% NaHCO$_3$/7% NaCl solution. The solids which formed were removed by filtration and washed with tetrahydrofuran (18 g). The aqueous layer was extracted with tetrahydrofuran (18 g). The combined tetrahydrofuran extracts were washed successively with a 1% Cysteine/2.5% NaHCO$_3$/7% NaCl solution and a 2.5% NaHCO$_3$/7% NaCl solution. Methanol (28 g) was charged and the solution concentrated to 28 g. Methanol (28 g) was charged and the product was allowed to crystallize. Methanol (28 g) was charged and the slurry was concentrated to 45 g. Methanol (60 g) was charged and the mixture concentrated to 75 g. The slurry was heated to 60° C. for 30 minutes and then cooled to ambient temperature. The solids were isolated by filtration, washed with methanol (2×8 gm) and vacuum dried at 50° C. to provide 4.42 g of the titled compound. $^1$H NMR (400 MHz, DMSO-D6) δ ppm 1.35 (s, 9 H) 2.99 (s, 3 H) 3.76 (s, 3 H) 5.62 (d, J=7.82 Hz, 1 H) 7.12-7.29 (m, 5 H) 7.51-7.65 (m, 3 H) 7.72 (d, J=7.82 Hz, 1 H) 9.83 (s, 1 H) 11.39 (s, 1 H). MS (APCI) m/e 470.1 (M+H)$^+$.

Example 8

Genotoxic Testing

As discussed above, compound I (including salts thereof) is useful as a drug for treating HCV in humans. Thus, it is important that it be so prepared that it is safe for administration to humans. As one skilled in the art would understand, one aspect of drug safety is the minimization of the amount of genotoxic impurities that are associated with the production of a given drug, and, can therefore also be present in the drug product. A couple of well established tests are used to measure the genotoxicity of chemical compounds. One such test is the computer-based Derek analysis, and the other—the Ames test, which is a biological assay that assesses the mutagenic potential of chemical compounds. As can be seen from the results below, the process for preparing compound I (or salt thereof) of this invention (shown in Schemes 3 and 4 below) results in the use and/or formation of fewer genotoxic impurities than the process shown in Schemes 1 and 2 below.

SCHEME 1

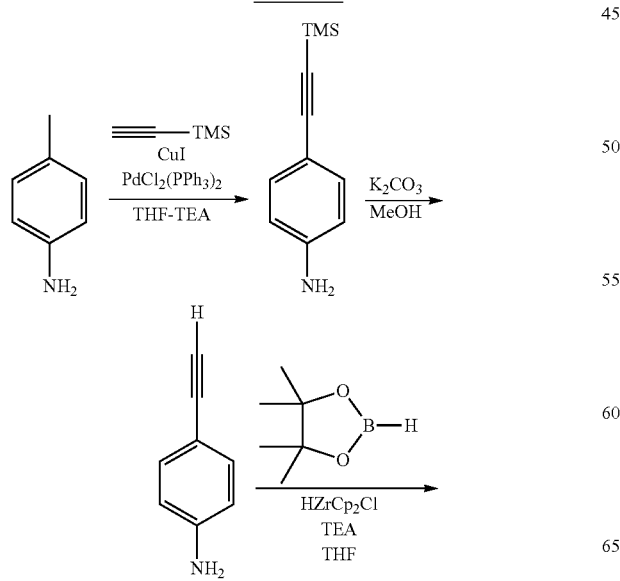

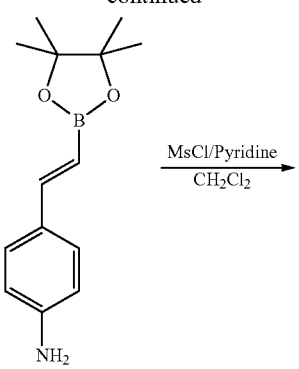

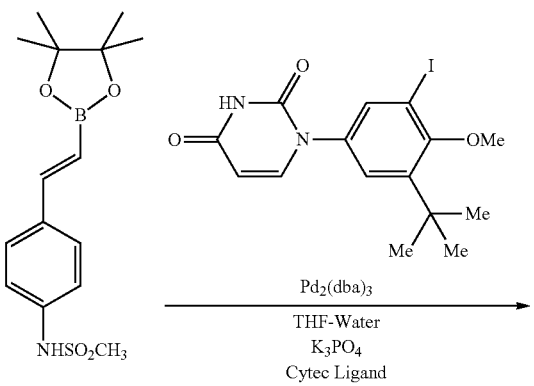

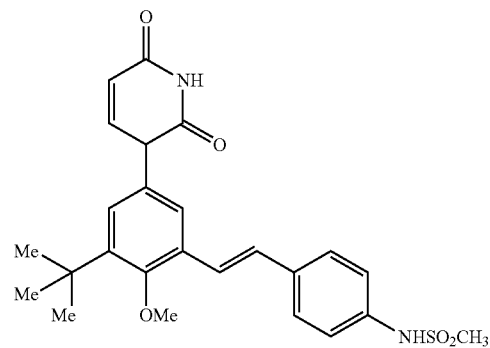

SCHEME 2

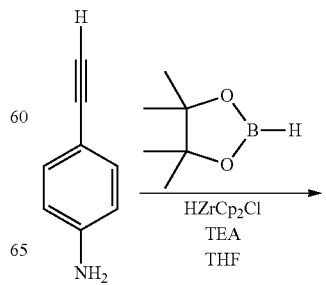

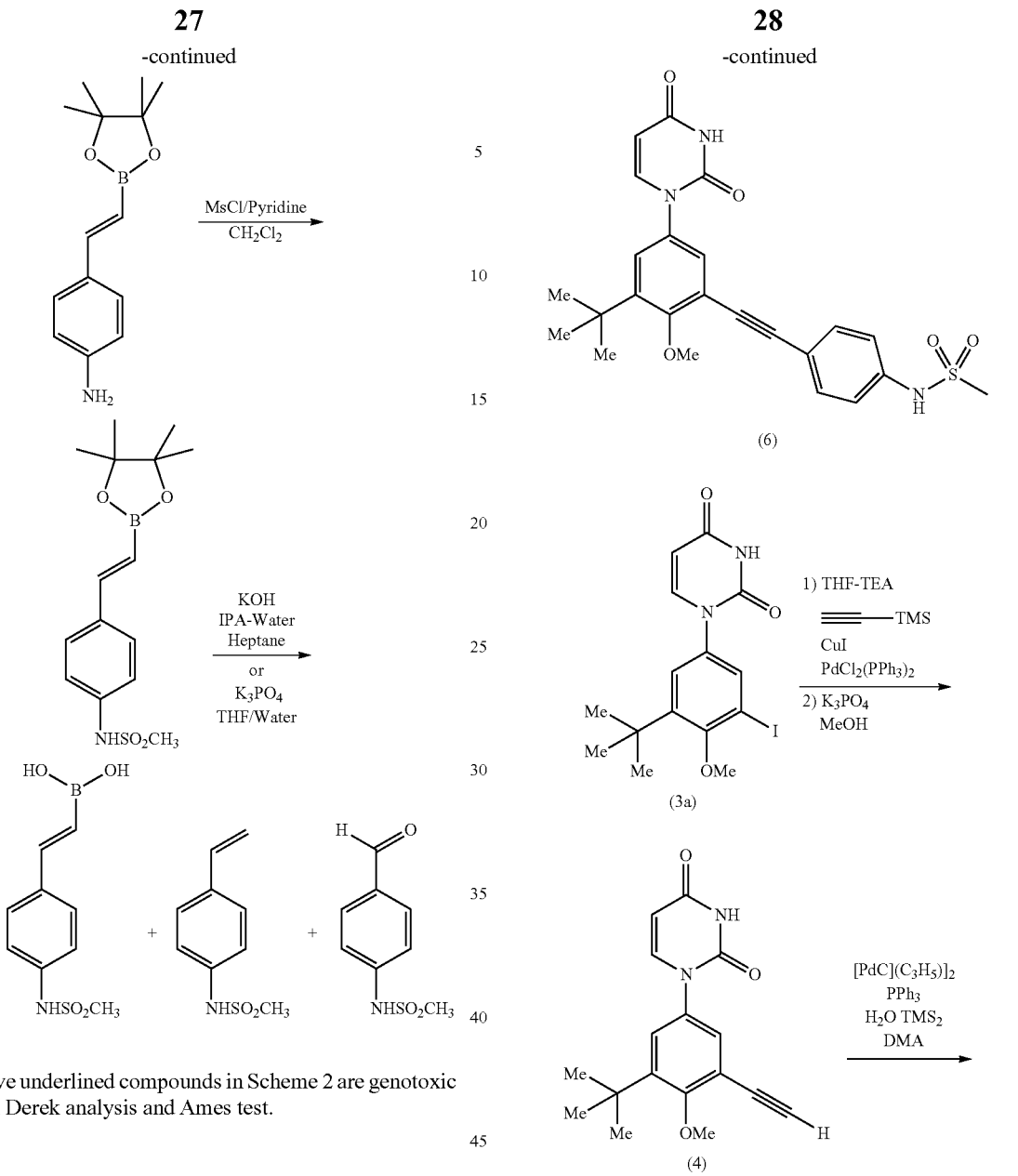
The five underlined compounds in Scheme 2 are genotoxic based on Derek analysis and Ames test.
SCHEME 3
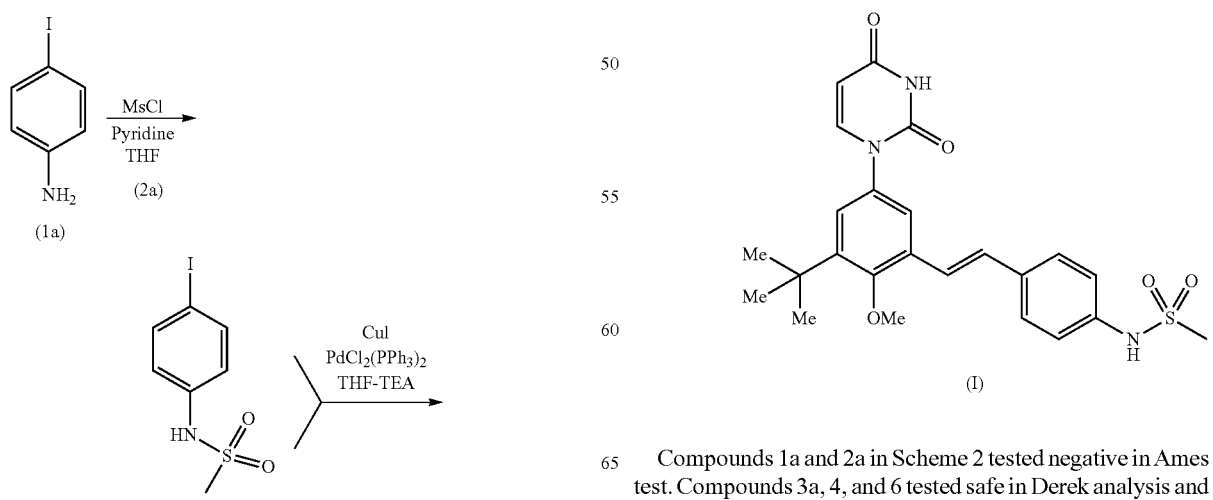
Compounds 1a and 2a in Scheme 2 tested negative in Ames test. Compounds 3a, 4, and 6 tested safe in Derek analysis and thus no Ames tests were performed.

SCHEME 4

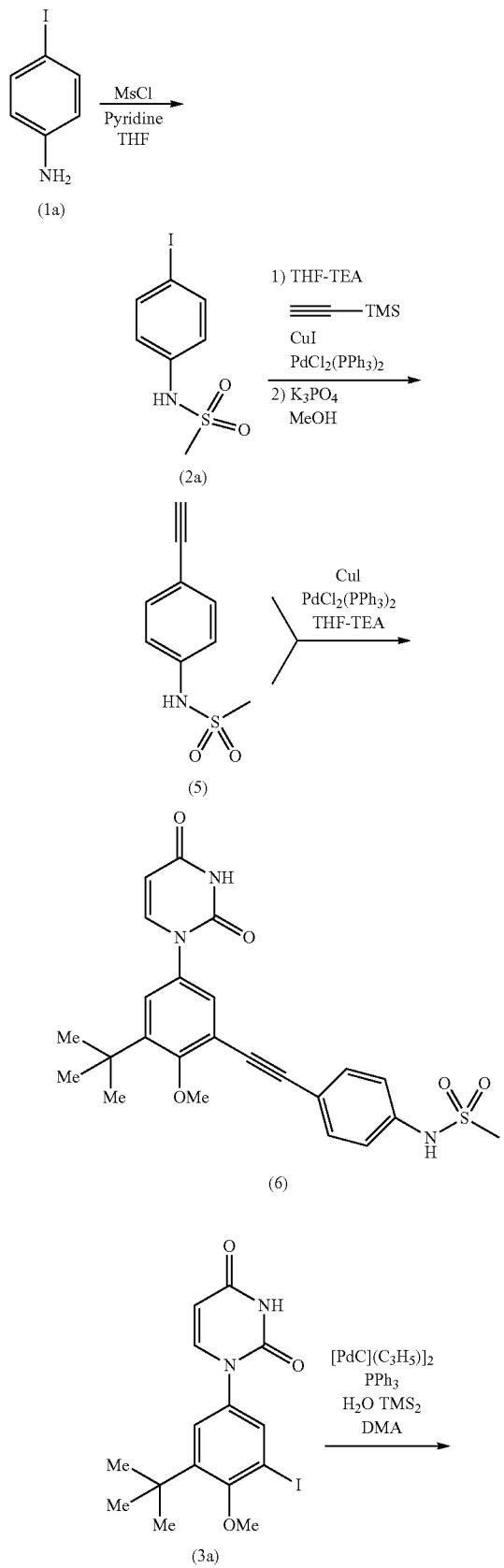

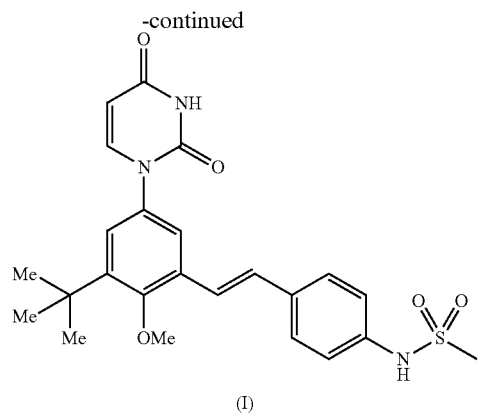

(I)

All references (patent and non-patent) cited above are incorporated by reference into this patent application. The discussion of those references is intended merely to summarize assertions made by their authors. No admission is made that any reference (or a portion of a reference) is relevant prior art (or prior art at all). Applicants reserve the right to challenge the accuracy and pertinence of the cited references.

We claim:

1. A process for preparing (E)-N-(4-(3-tert-butyl-5-(2,4-dioxo-3,4-dihydropyrimidin-1(2H)-yl)-2-methoxystyryl) phenyl)methanesulfonamide (compound I) or a salt thereof, wherein the process comprises:

reducing N-(4-((3-tert-butyl-5-(2,4-dioxo-3,4-dihydropyrimidin- 1(2H)-yl)-2-methoxyphenyl) ethynyl)phenyl) methanesulfonamide (compound 6) to (E)-N-(4-(3-tert-butyl-5-(2,4-dioxo-3,4-dihydropyrimidin-1(2H)-yl)-2-methoxystyryl)phenyl)methanesulfonamide (compound I) with a reductant comprising silane selected from the group consisting of triethylsilane, disilane, phenylsilane, diphenylsilane, tripropylsilane, triphenylsilane, tribenzylsilane, 1,1,1,3,5,5,5-heptamethyltrisiloxane, tributylsilane, di-tert-butylsilane, diethyloxysilane, dimethoxysilane, phenyldiethoxyethylsilane, dimethylsilane, halosilane, and tris(trimethylsilyl)silane in the presence of catalyst selected from the group consisting of allylpalladium(II)chloride, (triphenylphosphine)palladium(II)chloride, tetrakis(triphenylphosphine)palladium (0), dichlorobis(tri-o-tolylphosphine)palladium (II), palladium (II) acetate, [1,1'-bis(diphenylphosphino)ferrocene]dichloropalladium (II), tris(dibenzylideneacetone) dipalladium (0), dichloro(dibenzylideneacetone)dipalladium (II), dichlorotris(cyclohexylphosphine)-palladium (II), dichlorobis(triphenylphosphine) palladium (II), and chloro(η3-allyl)palladium(II) dimer-triphenylphosphine; and solvent selected from the group consisting of tetrahydrofuran, dimethylformamide, dimethylacetamide, N-methylpyrrolidone and combinations thereof:

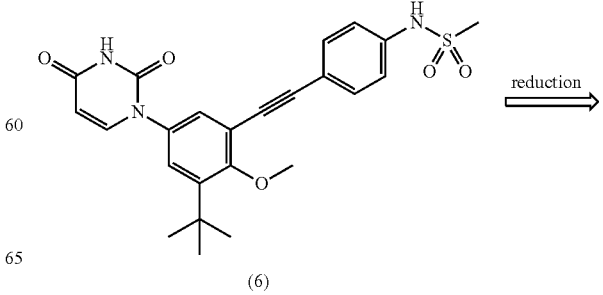

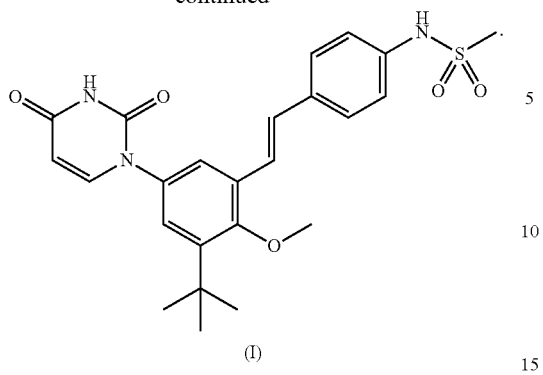

(I)

2. The process of claim 1, wherein the silane is selected from the group consisting of triethylsilane and 1,1,1,2,2,2-hexamethyldisilane.

3. The process of claim 1, wherein the silane is disilane.

4. The process of claim 3, wherein the disilane is selected from the group consisting of hexamethyldisilane, hexaphenyldisilane, 1,2-diphenyltetramethyldisilane, 1,2-dimethyl-1,1,2,2,-tetraphenyldisilane, 1,1,2,2-tetramethyldisilane, 1,2-diethoxy-1,1,2,2-tetramethyldisilane, 1,2-dimethoxy-1,1,2,2-tetramethyldisilane, and hexamethoxydisilane.

5. The process of claim 1, wherein the catalyst is palladium catalyst.

6. The process of claim 5, wherein the catalyst is selected from the group consisting of allylpalladium(II)chloride and chloro(η3-allyl)palladium(II) dimer-triphenylphosphine.

7. The process of claim 1, wherein the solvent is selected from the group consisting of tetrahydrofuran, dimethylacetamide, and a combination thereof.

8. The process of claim 1, wherein compound 6 is prepared by reacting 1-(3-tert-butyl-5-ethynyl-4-methoxyphenyl)pyrimidine-2,4(1H,3H)-dione (compound 4) with compound 2 selected from the group consisting of N-(4-iodophenyl)methanesulfonamide (compound 2a), N-(4-bromophenyl)methanesulfonamide (compound 2b), N-(4-chlorophenyl)methanesulfonamide (compound 2c), N-(4-[(arylsulfonyl)oxy]phenyl)methanesulfonamide (compound 2d), and N-(4-[(perfluoroalkylsulfonyl)oxy]phenyl)methanesulfonamide (compound 2e) in the presence of catalyst, base and solvent:

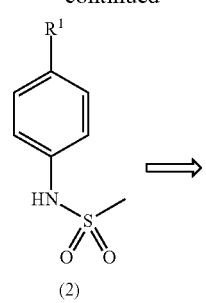

(2)

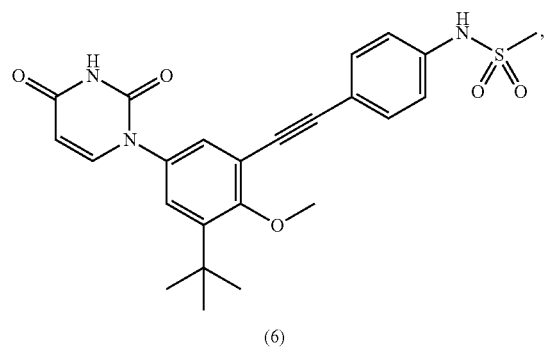

(6)

wherein R¹ is selected from the group consisting of halogen, arylsulfonyloxy and perfluoroalkylsulfonyloxy.

9. The process of claim 8, wherein the base is triethylamine.

10. The process of claim 8, wherein the solvent is tetrahydrofuran.

11. The process of claim 8, wherein compound 4 is prepared by:

reacting ethynyltrimethylsilane (≡─TMS)

(compound 7) with compound 3 selected from the group consisting of 1-(3-tert-butyl-5-iodo-4-methoxyphenyl)pyrimidine-2,4(1H,3H)-dione (compound 3a), 1-(3-bromo-5-tert-butyl-4-methoxyphenyl)pyrimidine-2,4(1H,3H)-dione (compound 3b), and 1-(3-tert-butyl-5-chloro-4-methoxyphenyl)pyrimidine-2,4(1H,3H)-dione (compound 3c) thus forming 1-(3-tert-butyl-4-methoxy-5-((trimethylsilyl)ethynyl)phenyl)pyrimidine-2,4(1H,3H)-dione (compound 8):

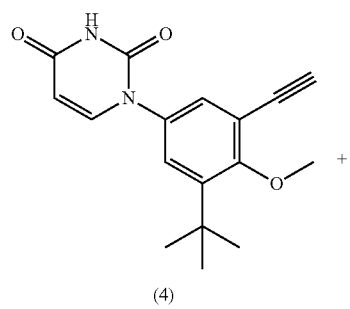

(4)

+

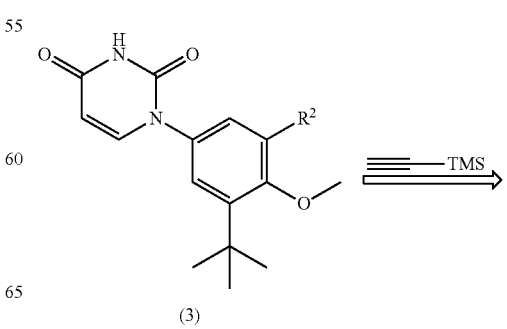

(3)

-continued

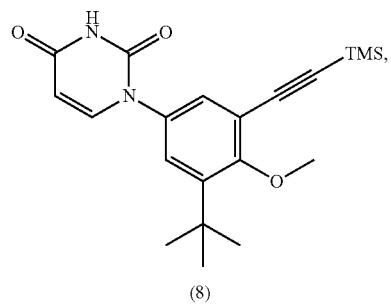

(8)

wherein R² is chlorine, bromine or iodine; and removing the trimethylsilyl (TMS) group from the formed 1-(3-tert-butyl-4-methoxy-5-(((trimethylsilyl)ethynyl) phenyl)pyrimidine-2,4(1H,3H)-dione (compound 8):

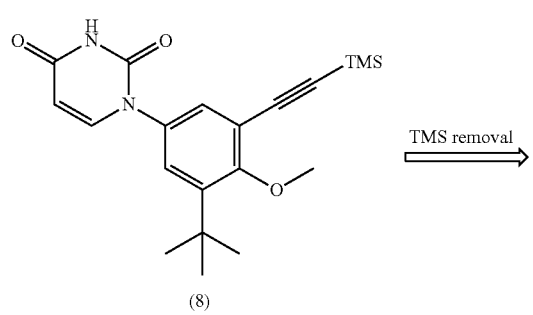

(8)

TMS removal ⟹

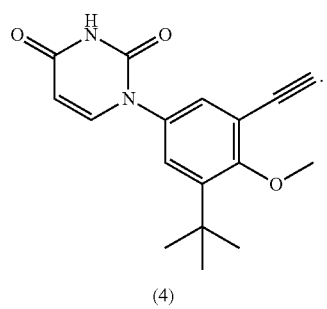

(4)

12. The process of claim 1, wherein compound 6 is prepared by reacting N-(4-ethynylphenyl)methanesulfonamide (compound 5) with compound 3 selected from the group consisting of 1-(3-tert-butyl-5-iodo-4-methoxyphenyl)pyrimidine-2,4(1H,3H)-dione (compound 3a), 1-(3-bromo-5-tert-butyl-4-methoxyphenyl)pyrimidine-2,4(1H,3H)-dione (compound 3b), and 1-(3-tert-butyl-5-chloro-4-methoxyphenyl)pyrimidine-2,4(1H,3H)-dione (compound 3c) thus forming N-(4-((3-tert-butyl-5-(2,4-dioxo-3,4-dihydropyrimidin-1 (2H)-yl)-2-methoxyphenyl)ethynyl)phenyl) methanesulfonamide (compound 6):

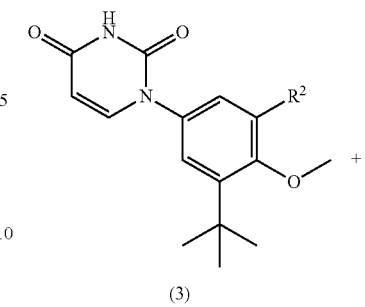

(3)

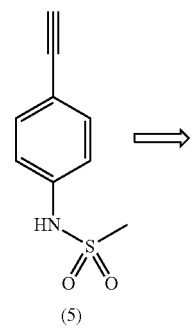

(5)

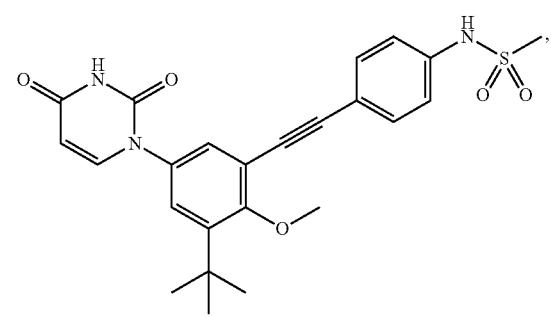

(6)

wherein R² is chlorine, bromine or iodine.

13. The process of claim 12, wherein compound 5 is prepared by:

reacting ethynyltrimethylsilane (≡—TMS)

(compound 7) with compound 2 selected from the group consisting of N-(4-iodophenyl)methanesulfonamide (compound 2a), N-(4-bromophenyl) methanesulfonamide (compound 2b), N-(4-chlorophenyl)methanesulfonamide (compound 2c), N-(4-[(arylsulfonyl)oxy] phenyl)methanesulfonamide (compound 2d), and N-(4-[(perfluoroalkylsulfonyl) oxy]phenyl) methanesulfonamide (compound 2e) thus forming N-(4-((trimethylsilyl)ethynyl)phenyl) methanesulfonamide (compound 9):

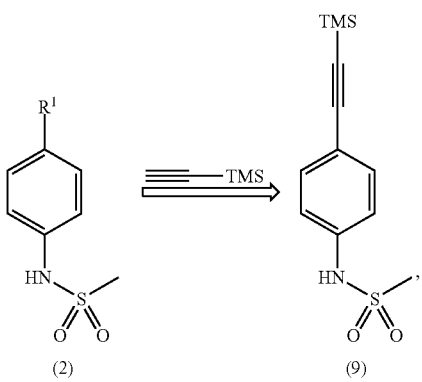

wherein R¹ is selected from the group consisting of halogen, arylsulfonyloxy and perfluoroalkylsulfonyloxy; and removing the trimethylsilyl (TMS) group from the formed N-(4-((trimethylsilyl)ethynyl)phenyl) methanesulfonamide (compound 9):

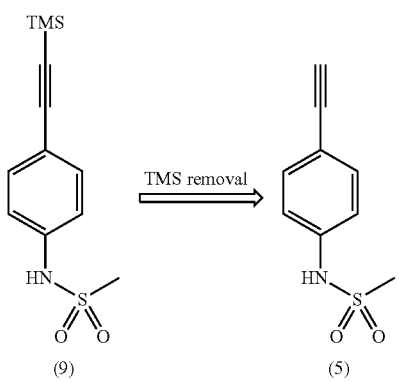

14. A process of preparing a compound having formula I

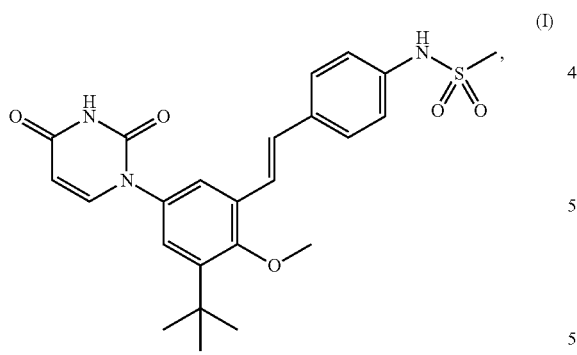

said process comprising:
reacting ethynyltrimethylsilane $$(\equiv\!\!-\!\!\text{TMS})$$

(compound 7) with compound 3 to form 1-(3-tert-butyl-4-methoxy-5-((trimethylsilyl)ethynyl)phenyl)pyrimidine-2,4(1H,3H)-dione (compound 8):

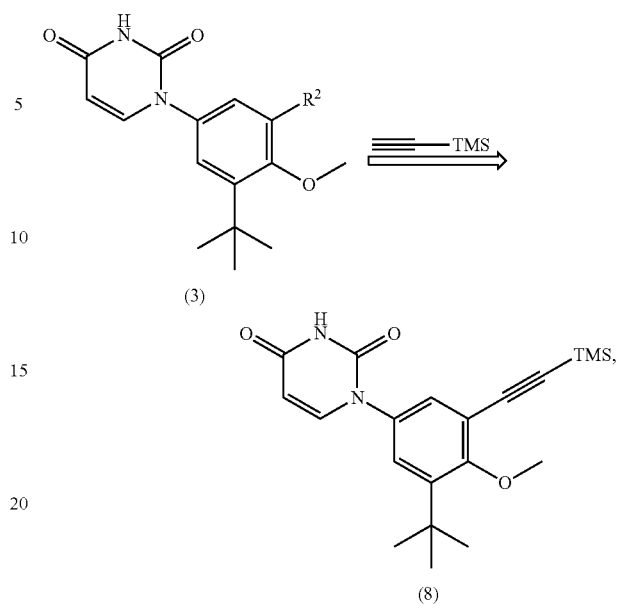

wherein R² is chlorine, bromine or iodine;

removing the trimethylsilyl (TMS) group from the formed 1-(3-tert-butyl-4-methoxy-5-((trimethylsilyl)ethynyl) phenyl)pyrimidine-2,4(1H,3H)-dione (compound 8):

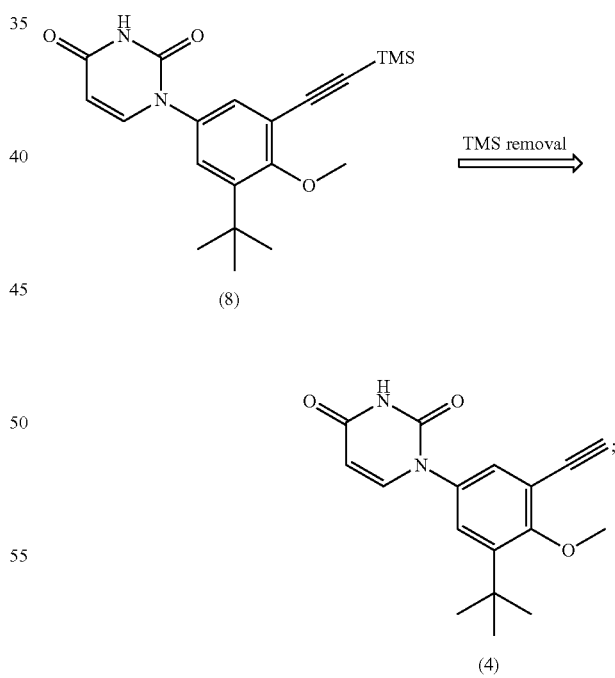

reacting 1-(3-tert-butyl-5-ethynyl-4-methoxyphenyl) pyrimidine-2,4 (1H, 3H)- dione (compound 4) with compound 2 in the presence of catalyst, base and solvent to form N-(4- ((3-tert-butyl-5-(2,4-dioxo-3,4- dihydropyrimidin- 1(2H)-yl)-2-methoxyphenyl) ethynyl)phenyl)methane sulfonamide (compound 6):

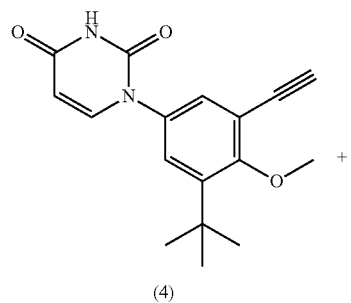

(4)

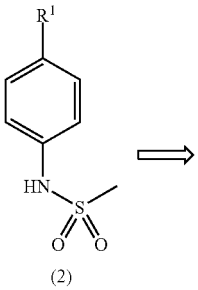

(2)

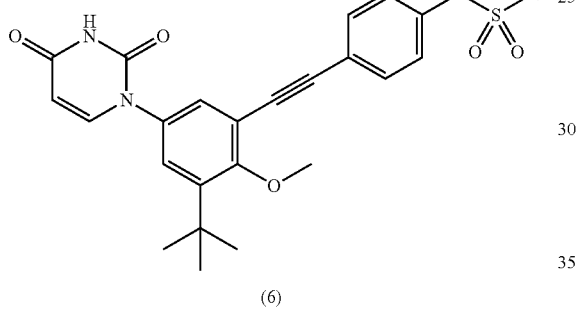

(6)

wherein R¹ is selected from the group consisting of halogen, arylsulfonyloxy and perfluoroalkylsulfonyloxy; and reducing compound 6 with a silane in the presence of catalyst and solvent:

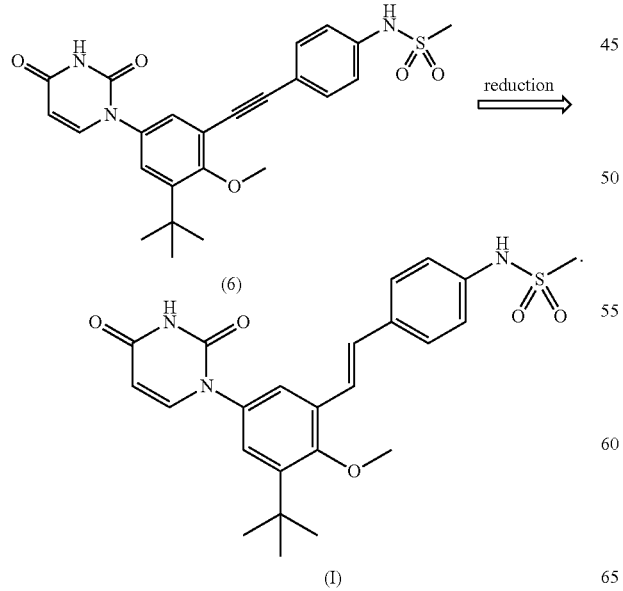

15. The process of claim 14, wherein compound 2 is selected from the group consisting of N-(4-iodophenyl)methanesulfonamide, N-(4-bromophenyl) methanesulfonamide, N-(4-chlorophenyl)methanesulfonamide, N-(4-[(arylsulfonyl)oxy]phenyl)methanesulfonamide, and N-(4-[(perfluoroalkylsulfonyl)oxy]phenyl)methanesulfonamide.

16. The process of claim 14, wherein compound 3 is selected from the group consisting of 1-(3-tert-butyl-5-iodo-4-methoxyphenyl)pyrimidine-2,4(1H,3H)-dione; 1-(3-bromo-5-tert-butyl-4-methoxyphenyl)pyrimidine-2,4(1H, 3H)-dione; and 1-(3-tert-butyl-5-chloro-4-methoxyphenyl)pyrimidine-2,4(1H,3H)-dione.

17. A process of preparing a compound having formula I

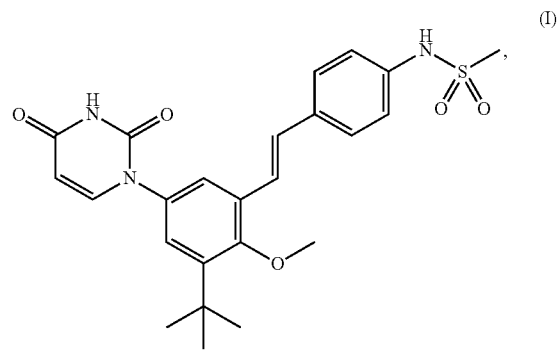 [SMILES: COc1c(/C=C/c2ccc(NS(C)(=O)=O)cc2)cc(-n2ccc(=O)[nH]c2=O)cc1C(C)(C)C]

said process comprising:

reacting ethynyltrimethylsilane ($\equiv$—TMS)

(compound 7) with compound 2 to form N-(4-((trimethylsilyl)ethynyl)phenyl)methanesulfonamide (compound 9):

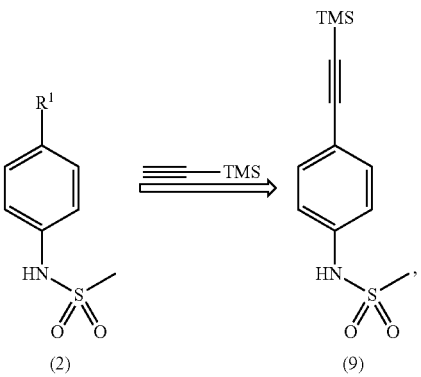

wherein R¹ is selected from the group consisting of halogen, arylsulfonyloxy and perfluoroalkylsulfonyloxy;

removing the trimethylsilyl (TMS) group from the formed N-(4-((trimethylsilyl)ethynyl)phenyl) methanesulfonamide (compound 9):

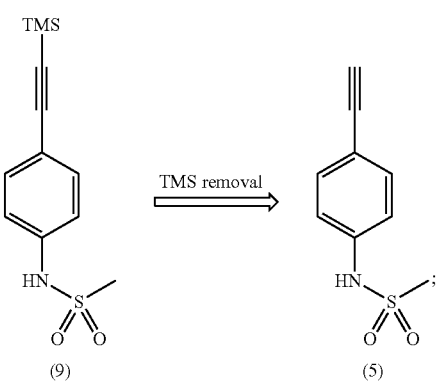 [SMILES: C[Si](C)(C)C#Cc1ccc(NS(C)(=O)=O)cc1 ; C#Cc1ccc(NS(C)(=O)=O)cc1]

reacting N-(4-ethynylphenyl)methanesulfonamide (compound 5) with compound 3 in the presence of catalyst, base and solvent to form N-(4-((3-tert-butyl-5-(2,4-dioxo-3,4-dihydropyrimidin-1(2H)-yl)-2-methoxyphenyl)ethynyl)phenyl)methanesulfonamide (compound 6):

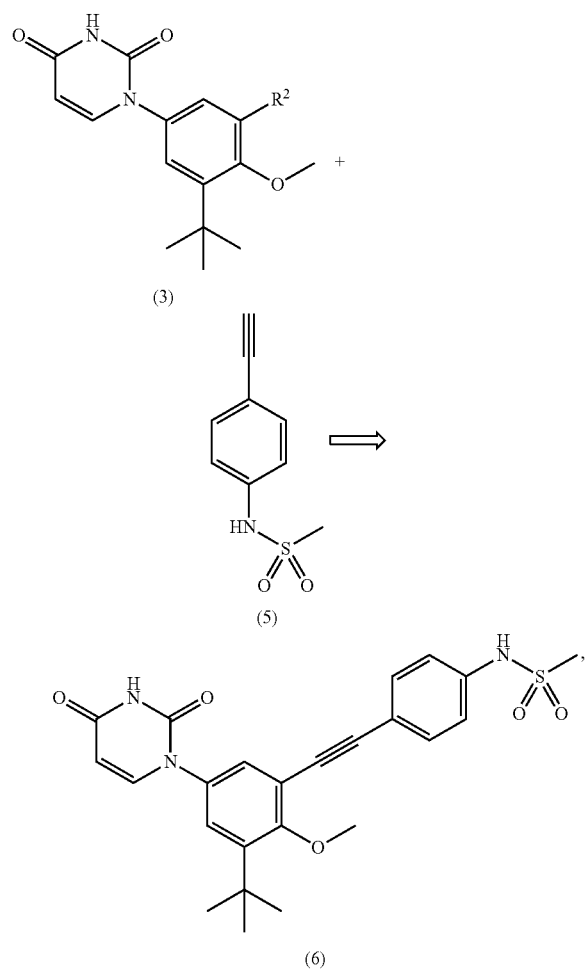

wherein $R^2$ is chlorine, bromine or iodine; and reducing compound 6 with a reductant comprising silane selected from the group consisting of triethylsilane, disilane, phenylsilane, diphenylsilane, tripropylsilane, triphenylsilane, tribenzylsilane, 1,1,1,3,5,5,5-heptamethyltrisiloxane, tributylsilane, di-tert-butylsilane, diethyloxysilane, dimethoxysilane, phenyldiethoxyethylsilane, dimethylsilane, halosilane, and tris(trimethylsilyl)silane in the presence of catalyst selected from the group consisting of allylpalladium(II)chloride, (triphenylphosphine)palladium(II)chloride, tetrakis(triphenylphosphine)palladium (0), dichlorobis(tri-o-tolylphosphine)palladium (II), palladium (II) acetate, 11,1'-bis(diphenylphosphino)ferroceneldichloropalladium (II), tris(dibenzylideneacetone) dipalladium (0), dichloro(dibenzylideneacetone)dipalladium (II), dichlorotris(cyclohexylphosphine)-palladium (II), dichlorobis(triphenylphosphine)palladium (II), and chloro(η3-allyl)palladium(II) dimer-triphenylphosphine; and solvent selected from the group consisting of tetrahydrofuran, dimethylformamide, dimethylacetamide, N-methylpyrrolidone and combinations thereof:

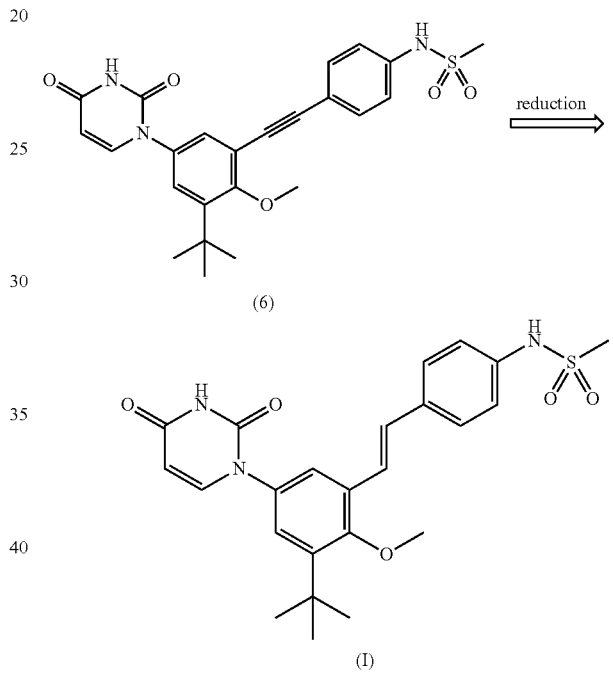

18. The process of claim 17, wherein compound 2 is selected from the group consisting of N-(4-iodophenyl)methanesulfonamide, N-(4-bromophenyl) methanesulfonamide, N-(4-chlorophenyl)methanesulfonamide, N-(4-[(arylsulfonyl)oxy]phenyl)methanesulfonamide, and N-(4-[(perfluoroalkylsulfonyl)oxy]phenyl)methanesulfonamide.

19. The process of claim 17, wherein compound 3 is selected from the group consisting of 1-(3-tert-butyl-5-iodo-4-methoxyphenyl)pyrimidine-2,4(1H,3H)-dione; 1-(3-bromo-5-tert-butyl-4-methoxyphenyl)pyrimidine-2,4(1H,3H)-dione; and 1-(3-tert-butyl-5-chloro-4-methoxyphenyl)pyrimidine-2,4(1H,3H)-dione.

20. The process of claim 8, wherein the catalyst is Cu(I) chloride or Cu(I) iodide and bis(triphenylphosphine)palladium(II)chloride.

21. The process of claim 14, wherein the catalyst is Cu(I) iodide and bis(triphenylphosphine)palladium(II)chloride.

22. The process of claim 14, wherein the base is triethylamine.

23. The process of claim 14, wherein the solvent is tetrahydrofuran.

24. The process of claim 17, wherein the catalyst is or Cu(I) iodide and bis(triphenylyphosphine)palladium(II)chloride.

25. The process of claim 17, wherein the base is triethylamine.

26. The process of claim 17, wherein the solvent is tetrahydrofuran.

* * * * *